(12) United States Patent
Frazier et al.

(10) Patent No.: US 6,169,394 B1
(45) Date of Patent: Jan. 2, 2001

(54) ELECTRICAL DETECTOR FOR MICRO-ANALYSIS SYSTEMS

(75) Inventors: A. Bruno Frazier; Richard D. Rabbitt; H. Edward Ayliffe, all of Salt Lake City, UT (US)

(73) Assignee: University of the Utah Research Foundation, SLC, UT (US)

( * ) Notice: Under 35 U.S.C. 154(b), the term of this patent shall be extended for 0 days.

(21) Appl. No.: 09/154,668

(22) Filed: Sep. 18, 1998

(51) Int. Cl.$^7$ .................................................. G01N 27/00
(52) U.S. Cl. ........................ 324/71.4; 324/692; 422/82.02
(58) Field of Search .................... 209/3.2, 12.2; 422/82.02; 324/71.4, 692

(56) References Cited

U.S. PATENT DOCUMENTS

| | | |
|---|---|---|
| 3,449,938 | 6/1969 | Giddings . |
| 3,811,841 * | 5/1974 | Kassel .................................. 324/71.4 |
| 4,147,621 | 4/1979 | Giddings . |
| 4,250,026 | 2/1981 | Giddings et al. . |
| 4,420,720 * | 12/1983 | Newton ................................ 324/71.4 |
| 4,737,268 | 4/1988 | Giddings . |
| 4,908,112 | 3/1990 | Pace . |
| 5,023,054 * | 6/1991 | Sato ..................................... 324/71.4 |
| 5,144,224 * | 9/1992 | Larsen ................................. 324/71.4 |
| 5,240,618 | 8/1993 | Caldwell et al. . |
| 5,464,581 * | 11/1995 | Engh ................................... 324/71.4 |
| 5,489,506 * | 2/1996 | Crane .................................. 209/12.2 |
| 5,605,662 | 2/1997 | Heller et al. . |
| 5,632,957 | 5/1997 | Heller et al. . |
| 5,871,158 | 2/1999 | Frazier . |
| 5,876,582 | 3/1999 | Frazier . |

OTHER PUBLICATIONS

Takashima et al., Frequency Domain Studies of Impedance Characteristics of Biological Cells Using Micropipet Technique, Biophysical Journal, vol. 54, pp. 995–1000, Dec. 1988.

Bao et al., Impedance Spectroscopy of Human Erythrocytes: System Calibration and Nonlinear Modeling, IEEE Transactions on Biomedical Engineering, vol. 40, No. 4, pp. 364–378, Apr. 1993.

Lo et al., Impedance Analysis of MDCK Cells Measured by Electric Cell–Substrate Impedance Sensing, Biophysical Journal, vol. 69, pp. 2800–2807, Dec. 1995.

Gimsa et al., Dielectric Spectroscopy of Single Human Erythrocytes at Physiological Ionic Strength: Dispersion of the Cytoplasm, Biophysical Journal, vol. 71, pp. 495–506, Jul. 1996.

Gale et al., Micromachined Electrical Field–Flow Fractionation ($\mu$–EFFF) System, IEEE Micro Electro Mechanical Systems Conference, Nagoya, Japan, Jan. 26–30, 1997.

Ayliffe et al., Micromachined Cellular Characterization System for Studying the Biomechanics of Individual Cells, 1997 International Conference on Solid–State Sensors and Actuators, Chicago, pp. 1307–1310, Jun. 16–19, 1997.

* cited by examiner

*Primary Examiner*—Safet Metjahic
*Assistant Examiner*—Jose M. Solis
(74) *Attorney, Agent, or Firm*—Workman, Nydegger & Seeley

(57) ABSTRACT

A micro-electric detector provides conductivity or impedance based measurements of a test sample placed in a microchannel of a micro-analysis system. The detector includes a pair of electrodes disposed on opposing sidewalls of the microchannel to create a detection zone in the microchannel between and adjacent to the electrodes. A variety of test samples can be monitored by the detector, such as particulate-containing fluids and biological materials including living cells and subcellular structures. The detector can be integrated on-chip using micromachining techniques with a variety of micro-analysis systems.

19 Claims, 13 Drawing Sheets

ELECTRICAL DETECTOR FOR MICRO-ANALYSIS SYSTEMS

BACKGROUND OF THE INVENTION

1. The Field of the Invention

The present invention relates generally to detector systems for measurement of the electrical characteristics of liquids, gases and biological materials. More specifically, the present invention relates to an electrical detector for micro-analysis systems capable of providing conductivity or impedance based measurements on a microscale of particulates in liquids or gases, and biological materials such as living cells.

2. The Relevant Technology

The electrical properties of cells, organelles, and protein solutions are of fundamental interest in the fields of biophysics, physiology, biotechnology, and medicine. Various electrical properties have previously been studied by a variety of methods such as pipette, dielectrophoretic, or electrorotational methods.

In the case of living organisms, pipette based methods suffer the disadvantage of being inherently invasive and require access to the intracellular space. Dielectrophoresis (DP) and electrorotation (ER) are relatively well established techniques for studying dielectric properties such as membrane capacitance and conductance, as well as cytoplasmic permittivity, of individual isolated cells. The DP and ER techniques measure the net force and torque which are generated when the substance of interest is placed in a nonuniform electric field. However, in order to extract the required information, namely the polarization vector, it is necessary to know both the electric field and the distribution of induced forces and moments. The actual electric field is dependent upon the geometry and the materials involved, and can be interpreted to some extent though the use of the measured data along with the appropriate electromagnetic model. The distribution of the internal forces and moments, however, can not be measured directly, but must be inferred from other information, such as a measurement of whole cell velocity, which can be subsequently analyzed using the Stokes approximation. This presents a problem in that a priori models describing the shape of the cell and the constitutive properties within the cell are required to estimate the dielectric parameters.

Recently, developments have been made in the area of microfabricated devices to more efficiently analyze the dielectric properties of small biological systems, particularly different types of cells. For example, a micro-ER device has been developed in which four gold electrodes are electroplated and oriented orthogonally on a glass wafer to create a recording zone on the surface of the wafer. Gimsa et al., *Biophysical Journal,* vol. 71, p. 495–506 (1996). Although this micro-ER device is capable of somewhat smaller spatial resolution, the device still suffers from the aforementioned difficulties generally associated with ER systems, and in addition, fails to resolve electrical characteristics on a subcellular level.

Electric impedance measurements have previously been demonstrated as an effective technique to characterize dielectric properties of tissues or cell suspensions. The electric impedance of tissues and cells is of interest in part because the impedance is known to vary with the morphology, histopathology, and electrophysiology of certain cells, and can therefore be used to monitor or detect certain pathological conditions or changes in the cells. Prior electric impedance measurement systems for cell layers and tissues have been developed. For example, an impedance sensing system has been developed which performs impedance spectroscopy, i.e., impedance variations in tissue and cell layers measured as a function of applied alternating currents (AC), typically in the range of 20 to 50,000 Hz. Lo et al., *Biophysical Journal,* vol. 69, p. 2800–2807 (1995). The sensing system was fabricated by sputtering gold onto thin polycarbonate sheets, and photolithography was used to delineate the desired gold patterns on the thin sheets and form the active electrode pairs. Although the Lo system is usefull in providing additional information on the resistive and capacititve properties of cells and cell membranes, the system fails to resolve electrical characteristics on a subcellular level.

Many of the recent medical and drug advances can be tied directly to improvements in chemical and biological analysis systems. These analysis systems are used to study all kinds of chemicals and biological molecules and to screen these particles for efficacy in various medical applications. Such techniques include electrophoresis, gas and liquid chromatography, the various biosensor devices that use proteins, DNA, antibodies, cells, and other biological particulates. Of critical importance to all of these techniques is the detection, monitoring, and transduction methods used to collect, observe, and interpret the signals, separation, or reaction generated by the device. Almost every method for energy transduction has been used to measure and observe signals in these various devices including optical, electrical, mechanical, thermal, chemical, magnetic and others. The most sensitive techniques and those generally used for the various analysis systems, and more specifically, chromatography systems, are optical measurements involving either fluorescence or UV absorption and reflection.

The optical techniques generally used with chromatography systems have several disadvantages. They are generally very bulky, expensive, complex, and often require modification of the sample being detected in order to perform measurements. These optical techniques are also very sensitive to physical movement and require considerable maintenance. While the UV extinction and light scattering techniques are quite robust and allow for a wide variety of sample types, they are also expensive and bulky. For large-scale labs with fixed laboratory equipment, these detection techniques provide high sensitivity and are well characterized and developed, but are not suitable for use with portable equipment, and especially for use with the new generation of microscale analysis systems.

In recent years, development has been made toward integrating a collection of microscale chemical and biological analysis systems on one chip, the so-called lab-on-a-chip design. A number of individual biological and chemical analysis techniques have been demonstrated in a micro-scale system and have been implemented using micromachining technology. These systems include electrophoresis, free-flow electrophoresis, electrical field-flow fractionation (EFFF), polymerase chain reaction (PCR), gas chromatography, liquid chromatography, and hybrid systems.

Unfortunately, most micromachined systems rely on off-chip components to perform the bulk of the detection and signal processing functions. These detection systems are generally the same as those used for the corresponding macro-analysis system with slight modifications for working on the smaller microscale systems. In many cases, after processing the sample using the microscale device, the sample is moved off chip for analysis. Moving the sample off-chip, though, can be very detrimental in terms of resolution for chromatography systems, and measurement quality for other systems.

Thus, there is a need for a simple, inexpensive, and micromachinable detection system with application to a variety of devices and manufacturable on a number of different surfaces.

SUMMARY AND OBJECTS OF THE INVENTION

It is a primary object of the present invention to provide a system for high resolution measurement of the electrical characteristics of biological systems such as cellular and subcellular structures, or of other very small samples of materials.

It is yet another object of the invention to provide a device for the detection of particles which have been separated by a biological or chemical micro-analysis system and which can be incorporated onto the same chip as the micro-analysis system.

A further object of the invention is to provide a conductivity or impedance detector device for particles which have been separated by micro-analysis systems which achieves a higher performance (e.g., increased resolution, decreased band broadening, etc.) than conventional off-chip detectors.

To achieve the forgoing objects and in accordance with the invention as embodied and broadly described herein, a micro-electric detector is provided for conductivity or impedance based measurements of a test sample placed in a microchannel of a micro-analysis system. The detector includes a pair of electrodes disposed on opposing sidewalls of the microchannel to create a detection zone in the microchannel between and adjacent to the electrodes. The detector can be utilized in a variety of micro-analysis systems such as micro-electric-impedance systems which utilize micro-electric sensors, electrical field-flow fractionation systems, chromatography systems, and the like. The detector is integrated on-chip with the micro-analysis system by micromachining techniques.

A micro-electric sensor device with an on-chip detector for use in a micro-analysis system according to one embodiment of the invention includes a substrate having a substantially planar upper surface. At least one microchannel is formed in the upper surface of the substrate and is defined by a pair of opposing sidewalls and a bottom wall in the substrate. One or more reservoirs are formed in the planar surface of the substrate and are in fluid communication with the microchannel. At least one pair of opposing detector electrodes are formed on the planar surface of the substrate and terminate at electrode tips formed on the opposing sidewalls of the microchannel such that the electrode tips face each other. This creates a detection zone in the microchannel between and adjacent to the electrodes such that the electrodes provide for transverse interrogation of a test sample in the microchannel by conductivity or impedance based measurements.

In another embodiment, a micromachined system for electrical field-flow fractionation ($\mu$-EFFF) of a fluid incorporates a detector on-chip according to the present invention. The $\mu$-EFFF system includes a microchannel device comprising a first substrate having a planar inner surface with an electrically conductive layer such as an electrode formed thereon. The system also includes a second substrate having a planar inner surface with an electrically conductive layer such as an electrode formed thereon. The second substrate is positioned over the first substrate so that the respective conductive layers of the first and second substrates face each other. An intermediate layer such as an insulating layer is interposed between the first and second substrates, with the intermediate layer being patterned to form opposing sidewalls of at least one microchannel. The conductive layers on the first and second substrates define opposing boundaries along the length of the microchannel. Inlet and outlet ports are formed in the first and/or second substrate to allow fluid flow into and out of the microchannel. A detector comprising at least one pair of opposing electrodes is formed on the inner surfaces of the first and second substrates adjacent to the outlet port. This creates a detection zone in the microchannel between and adjacent to the electrodes such that the detector can provide conductivity or impedance based measurements of a fluid sample in the microchannel.

A method for monitoring a test sample in a micro-analysis system according to the present invention includes providing a device with at least one microchannel and an associated detector electrode pair in the microchannel, and supplying electrical power to the electrodes to create an electric field in the detection zone of the microchannel between and adjacent to the electrodes. A test sample is injected into the microchannel and changes in the electric field are detected as the test sample enters the detection zone of the microchannel to provide conductivity or impedance based measurements of the test sample.

A variety of test samples can be monitored by the detector of the invention, such as particulate-containing fluids and biological materials including living cells and subcellular structures. The detector provides for subcellular spatial resolution in biological systems, and can be used to characterize the dielectric properties of a small sample of material or measure the concentration of particles which have been separated by a biological or chemical micro-analysis system.

These and other aspects of the present invention will become more fully apparent from the following description and appended claims, or may be learned by the practice of the invention as set forth hereinafter.

BRIEF DESCRIPTION OF THE DRAWINGS

In order to more fully understand the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE INVENTION

Figure 1:
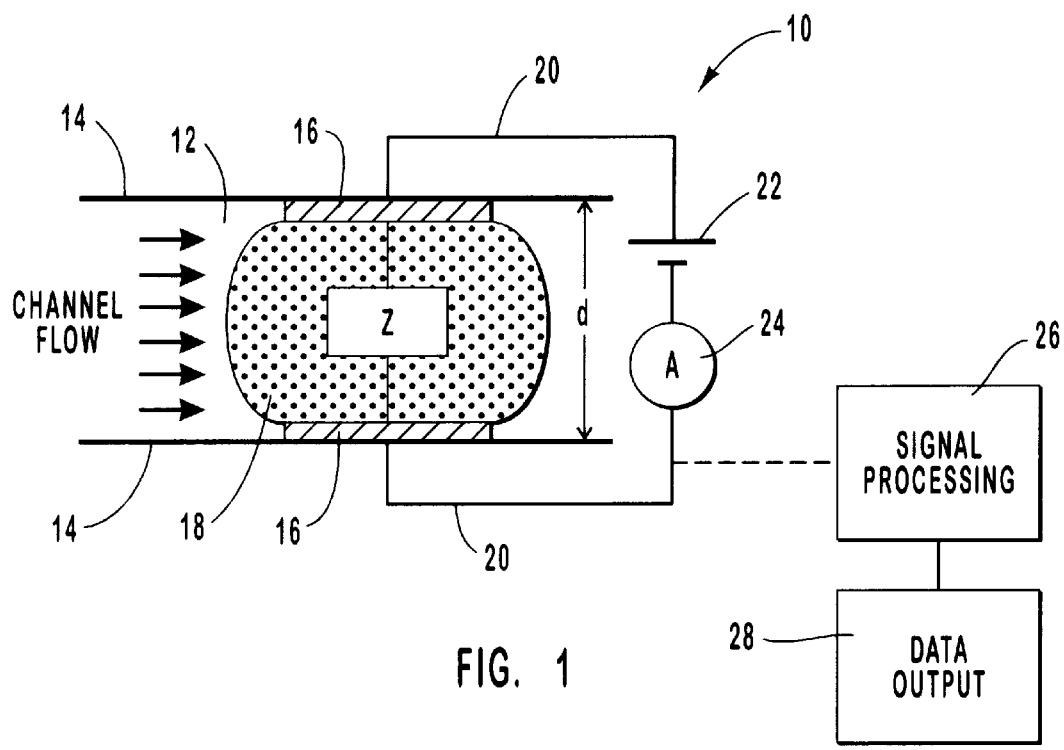
FIG. 1 is a schematic depiction of a detection system according to the present invention.

The present invention is directed to a low power micro-electric detector which can be utilized in a variety of micro-analysis systems. The detector can provide conductivity or impedance based measurements of a test sample placed in a microchannel of a micro-analysis system. The detector can be integrated on-chip to provide a conductivity or impedance based detection system for miniaturized biochemical analysis systems such as liquid chromatography systems, micro-electric-impedance systems which utilize micro-electric sensors, electrical field-flow fractionation systems, and the like.

The micro-electric detector of the invention is fabricated by micromachining techniques from biocompatible materials. As used herein, the term "micromachining" refers to techniques which are used in the electronics and microsensor fabrication industries, and includes the processes of etching, thin film deposition, lithographic patterning, and the like.

Referring to the drawings, wherein like structures are provided with like reference designations, the drawings only show the structures necessary to understand the present invention. Additional structures known in the art have not been included to maintain the clarity of the drawings.

FIG. 1 is a schematic depiction of a detection system 10 according to the present invention. The detection system 10 is formed in conjunction with a microchannel 12 in a micro-analysis system and provides conductivity or impedance based measurements. The microchannel 12 is defined by a first pair of opposing sidewalls 14 and a second pair of opposing sidewalls (not shown) adjacent to sidewalls 14. This provides microchannel 12 with a transverse cross-sectional profile that is substantially rectangular. The sidewalls of microchannel 12 are preferably composed of a biocompatible material. The microchannel 12 is preferably dimensioned such that the distance d between sidewalls 14 along the length of microchannel 12 is less than about 100 $\mu$m. The distance between the second pair of opposing sidewalls along the length of the microchannel can also be less than about 100 $\mu$m. In general, the aspect ratio of width to height for the microchannel varies from about 1:1 to about 300:1.

A first pair of low impedance detector electrodes 16 are formed on sidewalls 14 at a selected location along microchannel 12 such that electrodes 16 face each other. This creates a detection zone 18 in microchannel 12 between and adjacent to electrodes 16 when power is supplied to electrodes 16. The letter "Z" denotes the impedance to be measured in detection zone 18 of microchannel 12. The electrodes 16 can be formed form a variety of conductive materials such as titanium, gold, nickel, copper, iridium, platinum, palladium, carbon black, combinations and alloys thereof, and the like.

In an alternative embodiment, a second pair of electrodes can be disposed on the second pair of opposing sidewalls adjacent to electrodes 16. Such a configuration surrounds microchannel 12 with electrode pairs to provide tomography measurements of a test sample in the microchannel for two-dimensional imaging of the sample.

The microchannel 12 and associated detector electrodes 16 of detection system 10 are fabricated using conventional micromachining techniques. The microchannels can be formed by various processes such as etching, photolithographic, or printing processes. The electrodes can be formed by various processes such as physical vapor deposition or electrodeposition of a conductive material, followed by patterning. Such techniques allow detection system 10 to be incorporated into a variety of micro-analysis systems either as a conductivity detection system or an impedance spectroscopy based detection system.

A connection means such as conductive lines 20 are provided for electrically connecting electrodes 16 to a power source 22. The connection means can be any conductive structure or material such as electrical wires, conductive strips, and the like, which provides electrical connection. The conductive lines 20 also electrically connect electrodes 16 with a current meter 24 for data collection and analysis when detection system 10 is implemented as a conductivity detector.

Alternatively, conductive lines 20 can electrically connect electrodes 16 with a processing means such as an signal processing device 26 for analyzing a signal from electrodes 16. The processing means is utilized when detection system 10 is implemented as an impedance detector and can be a network analyzer, or other suitable signal processing device. A data output device 28 can be operatively connected to signal processing device 26 for displaying or printing data generated by the processor. The output device 28 can be various display or printing devices such as a scope device, video monitor, flat screen device such as a liquid crystal display (LCD), printer, plot device, and the like.

During operation of detection system 10, a small voltage, such as about 1 mv to about 10 volts, is applied from power source 22 across electrodes 16 and a direct current (DC)

and/or alternating current (AC) gradient is generated in detection zone 18. As the fluid sample carrying the particles of interest flows through microchannel 22 and into detection zone 18, any change in material between the electrodes will generally create a change in the measured current. With proper calibration, the concentration of the particles of interest or electrical characteristics of a biological sample can be determined through the amount by which the current changes as measured with current meter 24, or by analyzing the impedance with signal processing device 26.

Various micro-analysis system embodiments which employ the detector of the invention will be described as follows.

Figure 2A:
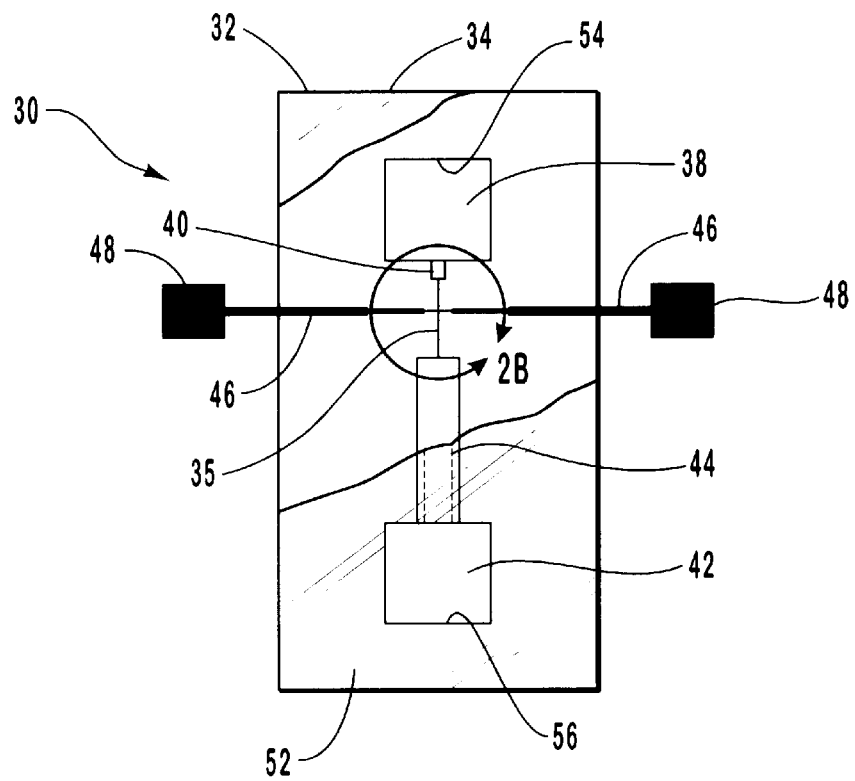
FIG. 2A is a schematic plan view of a micro-electric-impedance sensor device according to one embodiment which incorporates the detector of the invention.
Figure 2B:
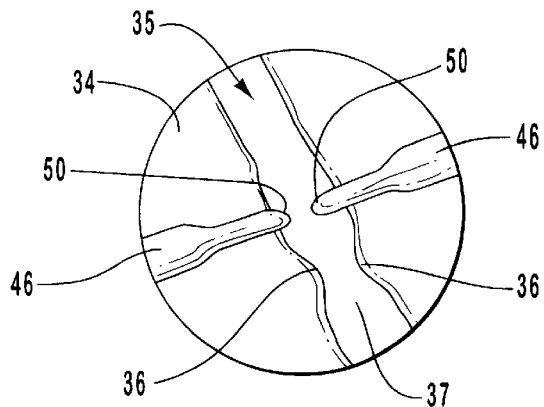
FIG. 2B is an enlarged sectional view of the sensor device of FIG. 2A.

FIG. 2A is a schematic depiction of a micro-electric-impedance (MEI) sensor device 30 according to one embodiment of the present invention. The sensor device 30 generally includes a substrate 32 having a substantially planar upper surface 34. The substrate 32 is preferably composed of glass, although other materials can be employed such as silicon, metals, plastics, and composites or combinations thereof. A microchannel 35 is formed in upper surface 34 of substrate 32 and is defined by a pair of opposing sidewalls 36 and a bottom wall 37 as shown in FIG. 2B. The microchannel 35 is preferably dimensioned to have a width between sidewalls of less than about 100 µm, and a height also less than about 100 µm.

The microchannel 35 is in fluid communication at one end thereof with a first reservoir 38, which is also formed in substrate 32. Preferably, reservoir 38 holds a buffer solution and is used for sample input such as for placement of cells to be tested. A first input channel 40 provides communication between microchannel 35 and reservoir 38. The microchannel 35 is also in fluid communication at an opposite end thereof with a second reservoir 42, which is also formed in substrate 32. Preferably, reservoir 42 is used for secondary solution input such as for placement of buffer solutions, chemotactants, or cell culture media. A second input channel 44 provides communication between microchannel 35 and reservoir 42.

A pair of detector electrodes 46 are formed on substrate 32 on opposing sides of microchannel 35 as depicted in FIGS. 2A and 2B. The detector electrodes 46 provide for transverse interrogation of a test sample such as a living cell by conductivity or impedance based measurements. A pair of opposing bond pads 48 which can be wired to a power source (not shown) are electrically connected to detector electrodes 46. The detector electrodes 46 extend from bond pads 48 across upper surface 34 of substrate 32 and are dimensioned to decrease in width as the electrodes approach each side of microchannel 35. Various conductive materials can be utilized to form electrodes 46, such as titanium, gold, nickel, copper, iridium, platinum, palladium, carbon black, combinations and alloys thereof, and the like.

Each of electrodes 46 terminate in an electrode tip 50 formed on opposing sidewalls 37 of microchannel 35 such that the electrode tips 50 face each other, as shown in FIG. 2B. The electrode tips 50 are exposed to the interior of the lumen of microchannel 35 such that the channel width between tips 50 is about 0.1 µm to about 100 µm. The area between and adjacent to the electrode tips 50 in microchannel 35 forms a detection zone for transverse interrogation of test samples. The microchannel 35 can have a cross-sectional area of about 15–300 µm² in the detection zone, which allows for passage of one cell at a time through the detection zone.

The microchannels, reservoirs, and electrodes in sensor device 30 are formed by conventional micromachining fabrication techniques.

A coverslip 52 such as a glass plate is attached to substrate 32 and forms the upper wall of microchannel 35 and input channels 40 and 44. A pair of access holes 54 and 56 are formed in coverslip 52 to provide fluid communication to reservoirs 38 and 42, respectively. Preferably, coverslip 52 is bonded to substrate 32 by a ultraviolet (UV) light curable, biocompatible adhesive to complete the structure of sensor device 10.

The sensor device 30 can be operatively connected to various conventional peripheral devices to provide an operative MEI system. These include injection devices and associated flow control devices for inputting test liquids into the reservoirs of device 30, as well as data processing and output devices. The sensor device 30 can be utilized as an impedance measuring system to determine the electrical characteristics of biological systems and can also be used to detect the presence of certain particles in solution samples as small as 1 femtoliter.

Figure 3A:
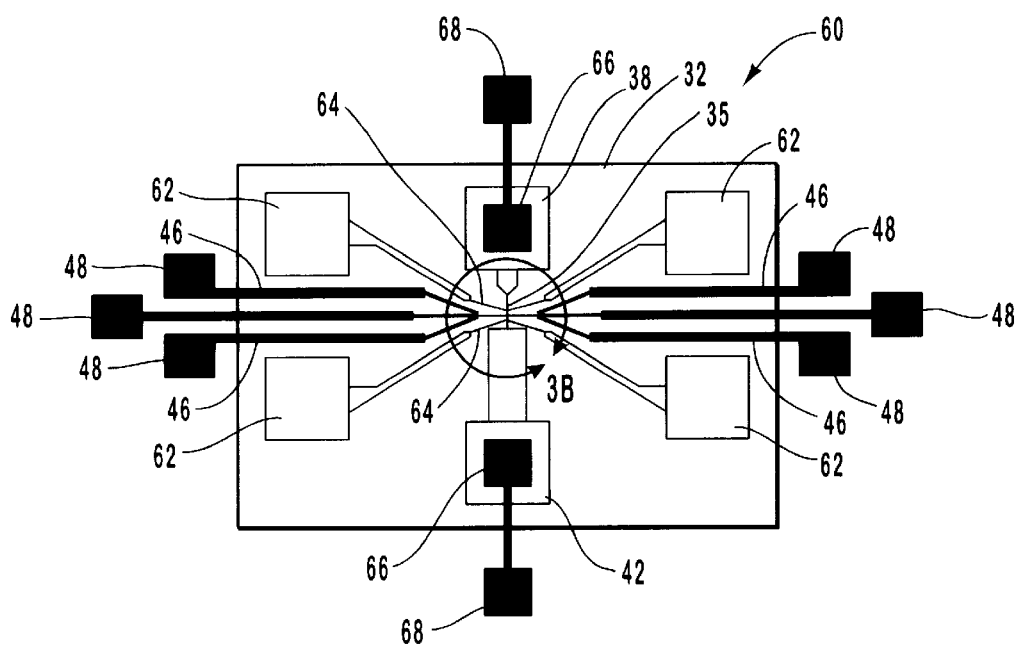
FIG. 3A is a schematic plan view of a micro-electric-impedance sensor device according to another embodiment which incorporates the detector of the invention.

FIG. 3A is a schematic depiction of an MEI sensor device 60 according to another embodiment of the present invention. The sensor device 60 includes similar components as sensor device 30 discussed above, including a substrate 32 having a substantially planar upper surface and a microchannel 35 formed in the upper surface of substrate 32. The microchannel 35 is in fluid communication at one end thereof with a first reservoir 38, which is also formed in substrate 32. The microchannel 35 is also in fluid communication at an opposite end thereof with a second reservoir 42, which is also formed in substrate 32.

A plurality of auxiliary reservoirs 62 are also formed in substrate 32 and are each in fluid communication with microchannel 35 through connecting microchannels 64. The auxiliary reservoirs 62 and connecting microchannels 64 allow for the introduction of various chemical agents into a test sample in microchannel 35, such as chemotactant agents (e.g., FMLP (fMet-Leu-Phe)) and/or pharmacological agents into distinct regions of a cell membrane for example.

Figure 3B:
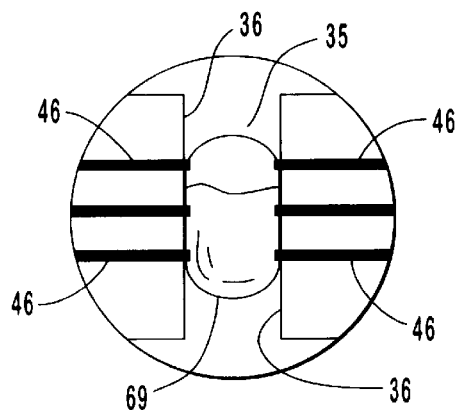
FIG. 3B is an enlarged sectional view of the sensor device of FIG. 3A.

A plurality of pairs of detector electrodes 46 are formed on substrate 32 on opposing sides of microchannel 35 as depicted in FIGS. 3A and 3B. The detector electrodes 46 provide for transverse interrogation of a test sample such as a living cell by conductivity or impedance based measurements. Each electrode 46 is electrically connected at one end to a bond pad 48 and terminates at the other end in an electrode tip formed on opposing sidewalls 36 of microchannel 35 such that the electrode tips face each other. The area between and adjacent to the electrode tips in microchannel 35 forms a detection zone for transverse interrogation of test samples. The tips of electrodes 46 are configured in such a manner as to be spatially separated along sidewalls 36 of microchannel 35 so as to span the length of a cellular structure 69 to be tested in microchannel 35, as shown in FIG. 3B.

In addition, a pair of reservoir electrodes 66 are formed in reservoirs 38 and 42 and are each electrically connected to a bond pad 68. The reservoir electrodes 66 allow for the application of longitudinal voltage potentials along microchannel 35 if desired. While sensor device 60 is shown in FIG. 3A as an eight electrode device, it should be understood that more or less electrodes may be utilized depending on the application desired. In general, the use of a plurality of detector electrode pairs provides for better spatial resolution of the measurements taken of a test sample in the microchannel.

The microchannels, reservoirs, and electrodes in sensor device 60 are formed by conventional micromachining fabrication techniques. A coverslip such as a glass plate with reservoir access holes is attached to substrate 32 and forms the upper wall of the microchannels in sensor device 60. The sensor device 60 can then be operatively connected to various conventional peripheral input and analysis devices for sample handling, data processing, and data acquisition to provide an operative MEI system.

The MEI sensor devices of the invention can be utilized in impedance measuring systems to interrogate the electrical characteristics of biological systems such as isolated cells located within the detection zone of the microchannel. During operation of the MEI sensor devices, an isolated cell is positioned in the microchannel for testing by suction or chemotactant motility. All of the regions of the cell pass by the electrode pairs in the microchannel, which enables electric impedance measurements to be carried out on the cell at subcellular spatial resolutions.

Figure 4A:
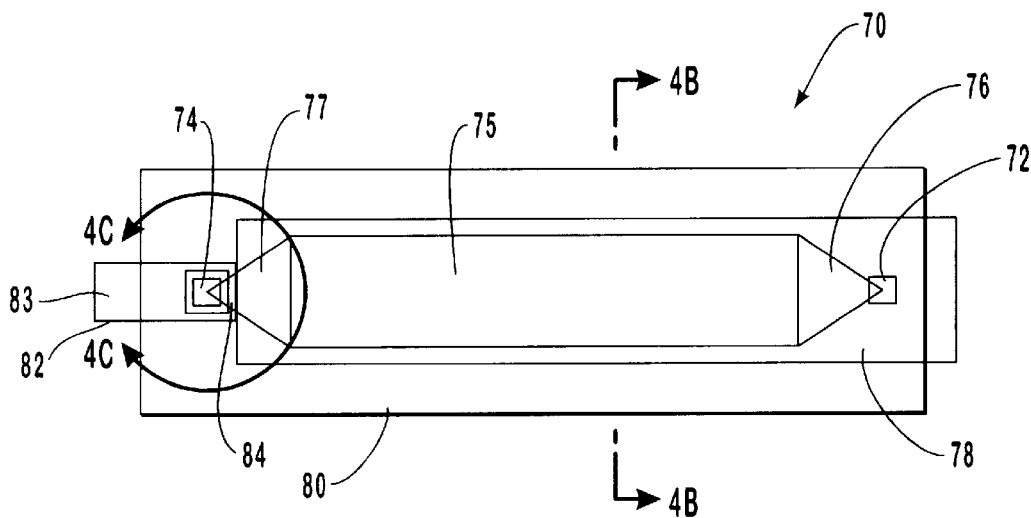
FIG. 4A is a schematic depiction of a microchannel device for a $\mu$-EFFF system which incorporates the detector of the invention.

The detection system of the invention can also be incorporated into a micro electrical field-flow fractionation ($\mu$-EFFF) system. FIG. 4A is a schematic depiction of a micromachined microchannel device 70 for a $\mu$-EFFF system which employs the detector of the invention. The device 70 includes an inlet port 72 and an outlet port 74, both in fluid communication with a microchannel 75. The microchannel 75 narrows at each respective end toward the ports, forming an angled input flow region 76 and an angled output flow region 77. A first conductive layer 78 forms one broad boundary of microchannel 75. An insulative layer forms sidewalls 80 around microchannel 75, forming a narrow boundary therearound. A detector is formed from a pair of opposing detector electrodes 82, which include bond pads 83 and detector strips 84 adjacent to outlet port 74. The detector strips 84 are formed across microchannel 75 in an on-chip configuration as shown best in FIG. 4C. While one detector strip 84 is shown in FIGS. 4A and 4C, it should be understood that the opposing detector strip is disposed on the opposite side of microchannel 75 in a configuration similar to that shown in FIG. 1.

Figure 4B:
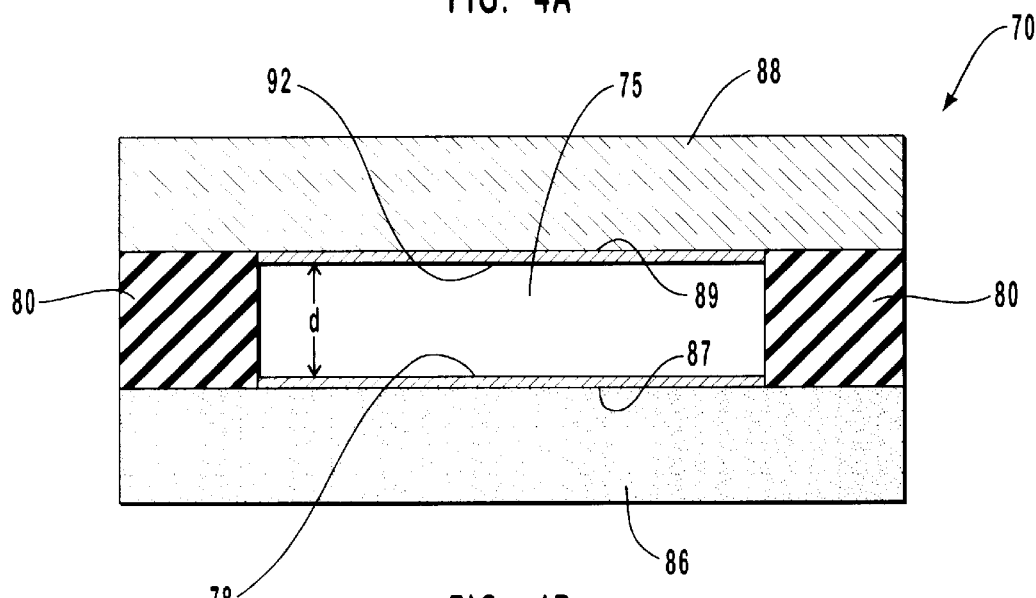
FIG. 4B is a schematic cross-sectional view perpendicular to fluid flow of the microchannel device of FIG. 4A.
Figure 4C:
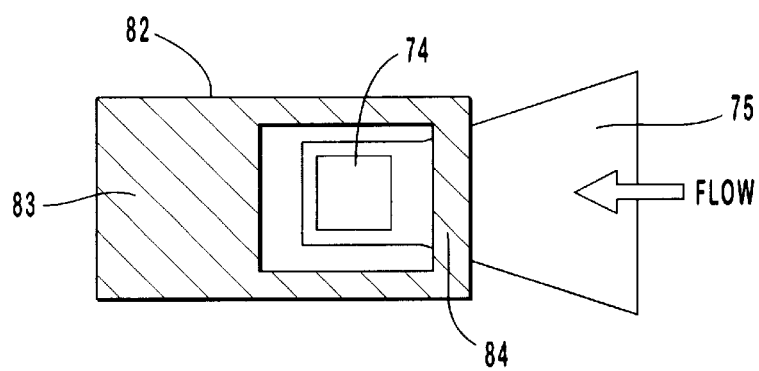
FIG. 4C is an enlarged sectional view of the microchannel device of FIG. 4A.

Additional structural components of microchannel device 70 are shown in FIG. 4B in a schematic cross-sectional view perpendicular to the flow. The microchannel device 70 includes a first substrate 86 having a substantially planar inner surface 87. The substrate 86 can be composed of a variety of materials including conductive materials, semiconductor materials such as silicon, nonconductive materials such as glass, plastic materials, and various composites or combinations thereof. A second substrate 88 is positioned over substrate 86 and is supported by opposing sidewalls 80. The substrate 88 has a substantially planar inner surface 89 and can be composed of a variety of materials such as those discussed above for substrate 86, including metals, silicon, glass, plastic materials, and the like. The substrates 86 and 88 can be composed of the same or different materials. The inlet port 72 and outlet port 74 can be formed on either or both of substrates 86 and 88.

The sidewalls 80 are formed from an intermediate layer deposited on substrate 86 and patterned at selected locations to form sidewalls 80 which define at least one microchannel 75. The intermediate layer forming sidewalls 80 is preferably an insulating material which can be selected from various biocompatible materials such as polyimides, acrylics, epoxies, photosensitive ceramics, photoresist materials, and combinations thereof A particularly preferred material for forming sidewalls 80 is a photosensitive polyimide material such as an imidized polyimide (e.g., Amoco 7055), which provides the advantages of excellent insulative properties, high mechanical and thermal stability, and also photosensitivity. The photosensitive property of this polyimide material allows for the precise formation of the sidewalls of the microchannel through standard ultraviolet lithographic patterning techniques.

The first conductive layer 78 is formed on inner surface 87 of substrate 86 between sidewalls 80 as depicted in FIG. 4B. A second conductive layer 92 is formed on inner surface 89 of substrate 88 between sidewalls 80 so as to face first conductive layer 78. The conductive layers 78 and 92 form electrode plates and are composed of one or more layers of a conductive material such as titanium, gold, nickel, copper, iridium, palladium, platinum, carbon black, combinations and alloys thereof, and the like. The conductive layers 78 and 92 define opposing continuous broad boundaries along the length of microchannel 75. When a voltage differential is applied to conductive layers 78 and 92, an electric field is induced across microchannel 75 along the length thereof.

The microchannel 75 can be dimensioned such that the distance d between conductive layers 78 and 92 along the length of microchannel 75 is less than about 100 $\mu$m. Advantageously, microchannel 75 can be dimensioned such that the distance d is about 40 $\mu$m or less, and even about 10 $\mu$m or less, because of the micromachining techniques used to fabricate microchannel device 70. The microchannel 75 has a transverse cross-sectional profile that is substantially rectangular, with the width of microchannel 75 substantially greater than the height (or distance d). The microchannel has an aspect ratio of width to height of at least about 20:1, and preferably at least about 80:1 for optimal performance of the $\mu$-EFFF system. Preferably, the microchannel has a width of about 100 $\mu$m to about 5 mm, and a height of about 1 $\mu$m to about 40 $\mu$m. The large aspect ratios are achieved through micromachining techniques, and provide better resolution in the separation of various particle species.

The detector strips 84 are formed on the inner surfaces of substrates 86 and 88 adjacent to outlet port 74 and conductive layers 78 and 92. This creates a detection zone in microchannel 75 between and adjacent to detector strips 84 such that the detector can provide conductivity or impedance based measurements of a fluid sample in microchannel 75. The detector electrodes are made of conductive materials such as titanium, gold, nickel, copper, iridium, palladium, platinum, carbon black, and combinations and alloys thereof. The detector is preferably interfaced via bond pads 83 with data processing and output devices such as a personal computer (not shown) for subsequent data analysis or a recording device such as a strip chart recorder. The computer can also be used to monitor and record data such as the applied voltage and current in the $\mu$-EFFF system.

The microchannel device 70 is connected to other conventional apparatus in order to form a fully functional $\mu$-EFFF system for the separation of molecules or particulates in solution. For example, the inlet port can be in fluid communication with a buffer reservoir, a pump, a sample input device, and a flow rate controller. The outlet port can be in fluid communication with a fraction collector or another downstream microchannel device.

The microchannel device 70 can be fabricated by conventional micromachining techniques with single or multiple microchannels therein for processing single or multiple test fluids. When a microchannel device is formed with a plurality of microchannels therein, a plurality of electrodes are formed on the substrates such that each microchannel is bounded by opposing electrode strips. In addition, a plurality of inlet and outlet ports are formed in the substrates for allowing fluid flow into and out of each microchannel. The multiple microchannels are operatively connected to a plurality of detectors, allowing for simultaneous multiple processing in either a parallel or serial analysis system. A method of fabricating a microchannel device for a μ-EFFF system is disclosed in a copending application Ser. No. 09/156,151 entitled "Micromachined Electrical Field-Flow Fractionation System" and filed on Sep. 18, 1998, the disclosure of which is incorporated herein by reference.

During operation of the μ-EFFF system, a voltage differential is applied to the conductive layers 78 and 92 in order to induce an electric field across microchannel 75. The applied voltage is about 0.5–3 volts, and preferably less than about 1.7 volts, in order to avoid the detrimental effects of electrolysis. A test fluid is injected through inlet port 72 and into microchannel 75, and the fluid is passed through the microchannel with the electric field therein in order to separate particles of different types in the fluid. The separated particles in the microchannel are monitored by the detector, and the fluid can be subsequently collected or further processed as desired.

The detector system of the invention operates under the assumption that the sample of interest being detected or measured has an impedance at least slightly different from that of the buffer solution carrying the sample. Thus, with a constant voltage applied across the detection zone, any change in the composition of the material between the electrodes will result in a change in the current through the detection circuit. This change in current can be measured in two ways: either by measuring the currently directly using a current meter or by converting the current to some other easily measured signal. The current in most cases will be carried by ions in the buffer solution and will therefore result in redox reactions at the electrodes that comprise the detector.

The impedance of the buffer solution can be changed in several different ways that are dependent on the parameters for operation of the system as well as the sample being detected. The first way that a sample might change the impedance in the detection zone is by being electrically conductive itself. In this case, the sample reduces the impedance in the detection area by carrying additional current itself. The opposite effect makes up the second way in which the impedance might change. If impedance of the sample is higher than that for the buffer solution then the effective impedance seen by the detector increases, thus making current conduction more difficult. A third way in which the impedance may change is by interference with the double layer of ions that build up at the electrode surface. The effect of the double layer is to reduce the current in the detector circuit substantially. In the event that the double layer is disturbed, either by dilution or being swept away, the current would be expected to rise in relation to the disturbance and then fall again as the disturbance is eliminated and steady state is reestablished. Thus, there are three general ways in which the impedance in the detection area might change and allow a sample to be detected. In most cases, it is expected that a combination of these modes will determine the actual change in impedance.

The establishment of a double layer on the detector electrodes can be modeled as a first order system with a time constant, τ. This time constant is most easily seen when a step in voltage is applied to the system. There is an immediate jump in current to some nominal value predicted using Ohm's law followed by an exponential decay in current to some steady state value dependent on the double layer thickness. Thus, assuming that a disturbance in the double layer occurs when most samples enter the detection area, the reestablishment of steady state will impact how quickly the detector can follow a "falling" signal. It should be noted here that the time constant as defined here for the detector is somewhat different from that generally used in instrumentation which measures how quickly the detector responds to changes in the input signal. Since the input here is generally a change in concentration of one analyte or another, it is extremely difficult if not impossible to know the input signal with any accuracy due to diffusion, convection, and other mixing agents and so it is extremely difficult to measure the time constant of the detector as it is normally defined. Since the time required for the instrument to follow a change in impedance is so small as to be insignificant, and any disturbance in the double layer can be considered to happen relatively quickly if not instantaneously, the only effect with potential to corrupt the measurement of the signal in the detector itself is the reestablishment of the double layer. Thus, the time required for reestablishment of steady state can be considered the limiting factor in terms of bandwidth for the detector.

One potential difficulty associated with the present detector in aqueous solutions is the electrolysis of water into hydrogen and oxygen. While the hydrogen and oxygen themselves do not cause a problem, the bubbles formed tend to increase noise in the detector and it has been demonstrated that a large jump in current occurs at the point that electrolysis begins. Since the current change due to samples moving through the detector is expected to be in the nano-ampere range, a large baseline current may make it difficult if not impossible to measure any signal on top of a large baseline current potentially in the microampere range. Thus, electrolysis needs to be avoided.

Of critical importance in chromatography systems is resolution and peak broadening. Resolution is a measure of how well a separation has been performed and peak broadening is a measure of how much a sample peak widens during its traversal of the separation channel. The detector used in the chromatography system can play a critical role in determining the amount of peak broadening that takes place. Mixing in the separation channel, which typically occurs in bands, expansions and contractions, or sharp geometries, is the usual cause for peak broadening. Structures of this type must be avoided, and the easiest way to do so is by placing the detector on-chip. Peak broadening is typically measured in terms of plate heights: a term related to the length of a channel required to perform an incremental amount of separation. The lower the plate height, the more powerful the instrument.

The detection system of the present invention provides many benefits and advantages over prior detectors. Some of the advantages of the detector include simplicity of design and operation, fast response and short warm-up time, high signal-to-noise ratio, detection of a wide range of sample types, small size, and compatibility with micromachining processes and very large scale integration (VLSI) technology for signal processing. The detector can be employed in a wide range of applications and allows detection of a wide range of analytes.

In particular, the detection system of the invention provides for high resolution measurement of the electrical characteristics of biological systems, as wells as other small samples of materials in liquids or gases as small as 1 femtoliter, which have been separated by a biological or chemical micro-analysis system. By incorporating the detector onto the same chip as the micro-analysis system, the detector can achieve a higher degree of resolution than conventional off-chip detectors. The detector can monitor the presence and the concentration of various types of particles which have been separated by a micro-analysis system and easily detects particles in the working concentration range of a separation system at low applied voltages. The detector can operate at higher (radio) frequencies and can be used to characterize the dielectric properties of a test sample.

A variety of test samples can be monitored by the detector of the invention through measuring conductivity or impedance variations in a microchannel, such as particulate-containing fluids and biological materials including living cells and subcellular structures. The detector allows for the noninvasive interrogation of cellular materials and provides for subcellular spatial resolution of a sufficient degree so as to resolve subcellular variations in impedance. Microsensor devices that employ the detector of the invention control membrane potentials using DC while interrogating membrane properties at radio frequencies. Such devices also provide for a simpler method of conducting cellular physiology studies involving pharmaceutics and/or the passive and excitable properties of cells.

The detector of the invention is particularly suited for impedance spectroscopy measurements of individual cells and subcellular structures. By measuring the variation of electrical impedance of a cell as a function of frequency, and subsequently combining the data with an appropriate electromagnetic model, the constitutive properties of the major cellular components can be determined. Also, different cell types display different peak impedances as a function of frequency. Thus, the detector can also distinguish among different cell types, as well as between normal and abnormal (e.g., diseased) cells.

The following examples are given to illustrate the present invention, and are not intended to limit the scope of the invention.

EXAMPLE 1

The MEI sensor devices of the invention can be fabricated by the following procedure. To begin fabrication, titanium and/or gold seed layers are deposited and patterned onto glass wafers (Pyrex 7740, from Corning), followed by spin application of a 5 $\mu$m layer of an epoxy-based photoresist (SU-8, from Microlithography Corp.). Metal electrode channels and fluid reservoirs are then patterned by contact lithography equipment (EV 420 from Electronic Visions). Electrode surfaces are then electroplated to a height of about 4 $\mu$m, and the photoresist is hardbaked. The wafers are then sputter coated with a 6000 Å layer of aluminum with a sputtering system (Discover 18, from Denton Vacuum). Photoresist is then spun on the aluminum layer and exposed with an appropriate mask to form the reservoirs and channels. The aluminum layer is then wet etched, followed with an oxygen-plasma etch (MP Plasma Lab System, from Oxford Instruments) to complete the formation of the reservoirs and channels.

Glass coverslips are provided to form the top surface of the channels. The glass is sputter coated with chromium and gold on both sides. Photoresist (PR 1813, from Shipley) is spun on both sides and patterned. The metals are then etched to expose regions of the glass to be removed. Rectangular holes are wet etched using a 50% HF solution and water. The holes allow access for the placement of cells, solution, and for the application of mechanical suction or pressure. The completed glass cover slips are aligned under a microscope with the base sensor devices on the wafer. The cover slips are then attached by applying a slight downward pressure while applying an ultraviolet light curable PVC adhesive (e.g., Loctite 3301) with a microdispenser (Microfil 34, from WPI). The adhesive is allowed to wick under the glass to the edge of the channels and reservoirs prior to UV activation. Small glass nipples can be bonded over the access holes in the coverslips to facilitate attachment of flexible tubing.

EXAMPLE 2

Two electrode MEI sensor devices were fabricated utilizing micromachining techniques. The sensor devices had small rectangular microchannels with typical cross-sectional areas of about 30 $\mu m^2$. Epoxy-based photoresist was used to form cell suspension reservoirs and the sidewalls of the microchannels in a glass substrate. Gold electrodes were electroplated to instrument the microchannels with a detection zone and had electrode tips with a cross-sectional area of about 20 $\mu m^2$. Glass coverslips with rectangular access holes were attached over the top of the microchannels.

Figure 5A:
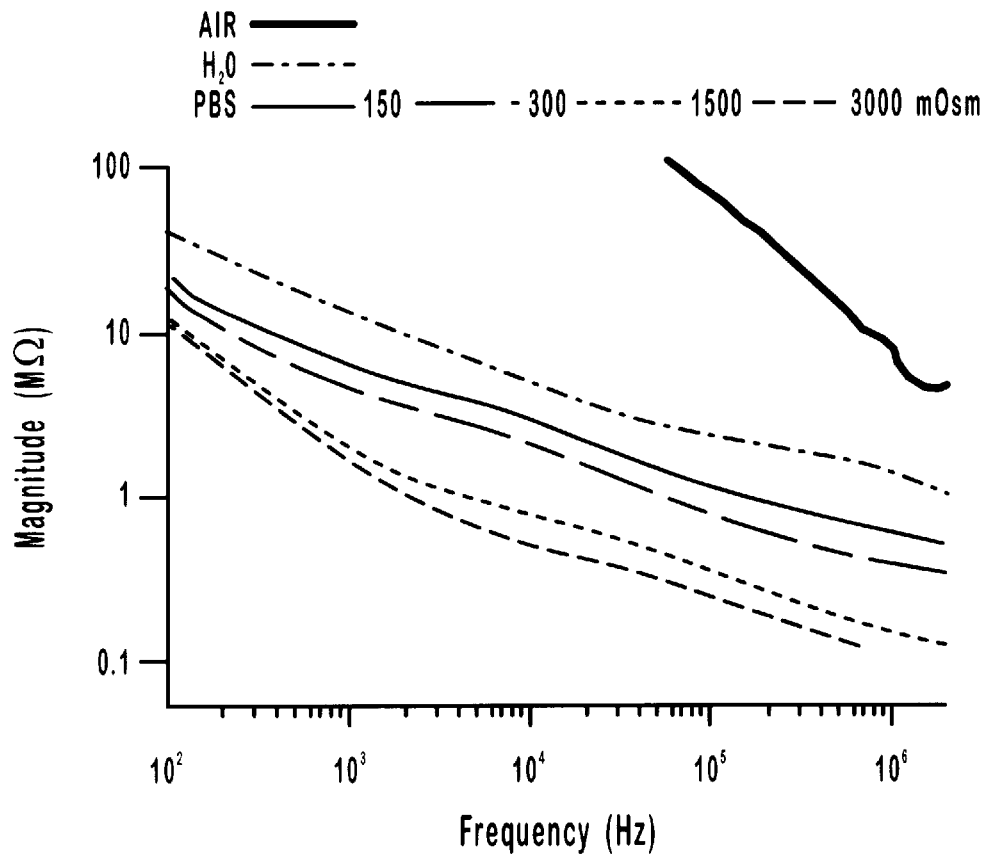
FIGS. 5A–5F are graphs showing the results of electric impedance measurements for a range of frequencies with a micro-electric-impedance sensor device of the invention.
Figure 5B:
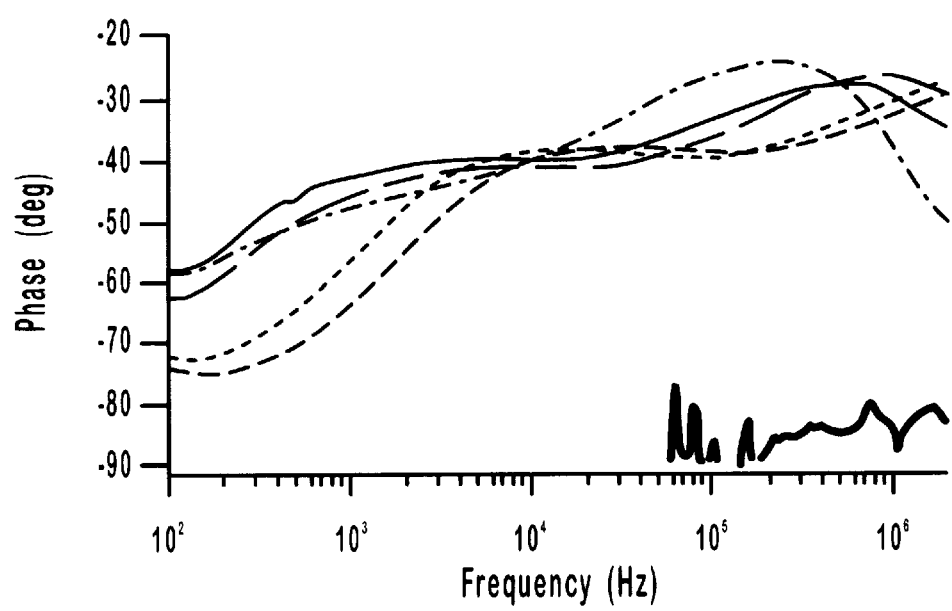

The overall electrical impedance (Z) of the devices was measured between the gold electrode tips at frequencies swept in the range from 100 Hz to 2 MHz using an HP 4194 network analyzer from Hewlett-Packard (HP). The measured impedance is a function of the geometry and properties of the devices, as well as the interactions in the cell/media in the detection zone. The devices were characterized by measuring Z for several isotropic materials placed in the microchannels and having known dielectric properties. Example results are depicted in the graphs of FIGS. 5A and 5B for air, partially deionized water, and several concentrations of phosphate buffer solution (PBS). It should be noted that the devices acted nearly as ideal capacitors when filled with air, but had a much more complex behavior when filled with physiological concentrations of PBS.

Figure 5C:
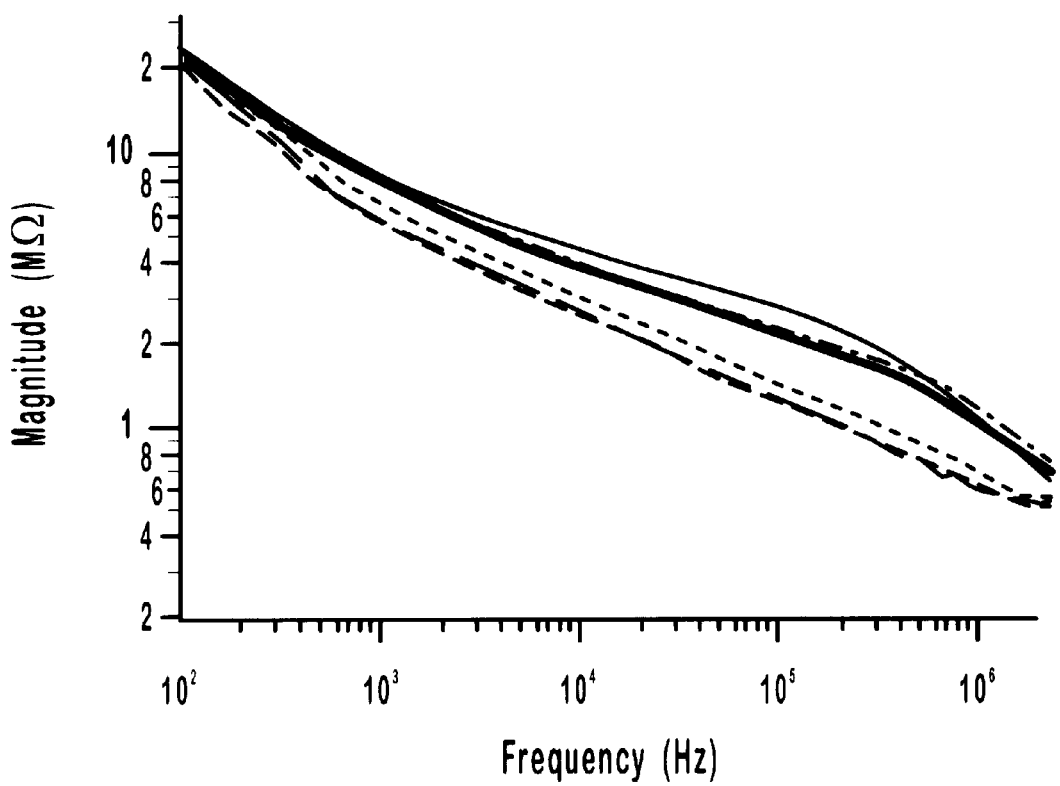
Figure 5D:
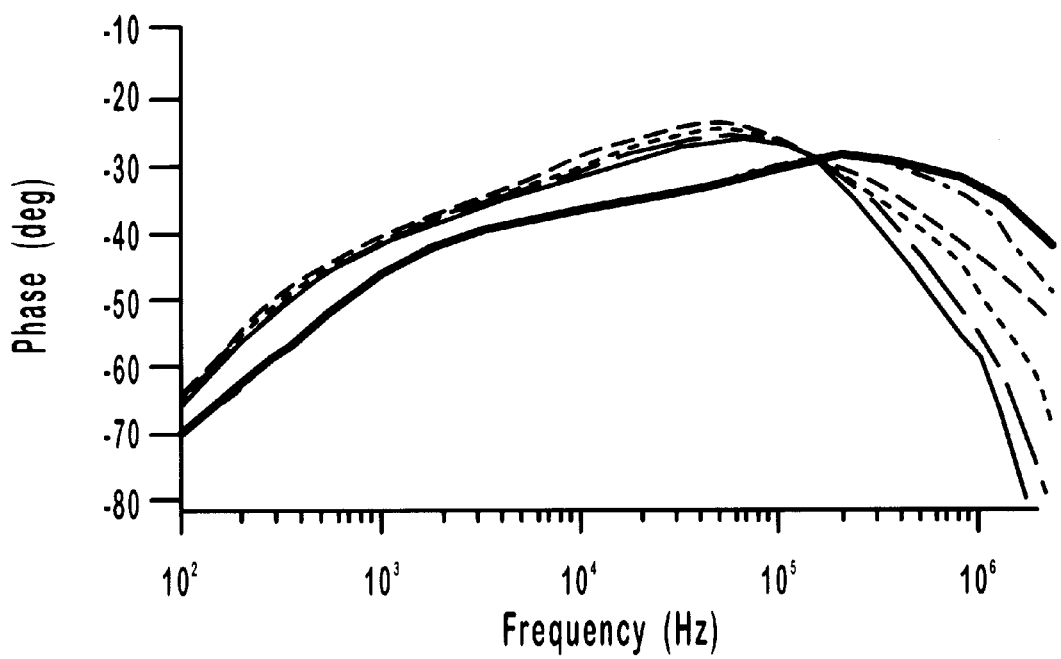
Figure 5E:
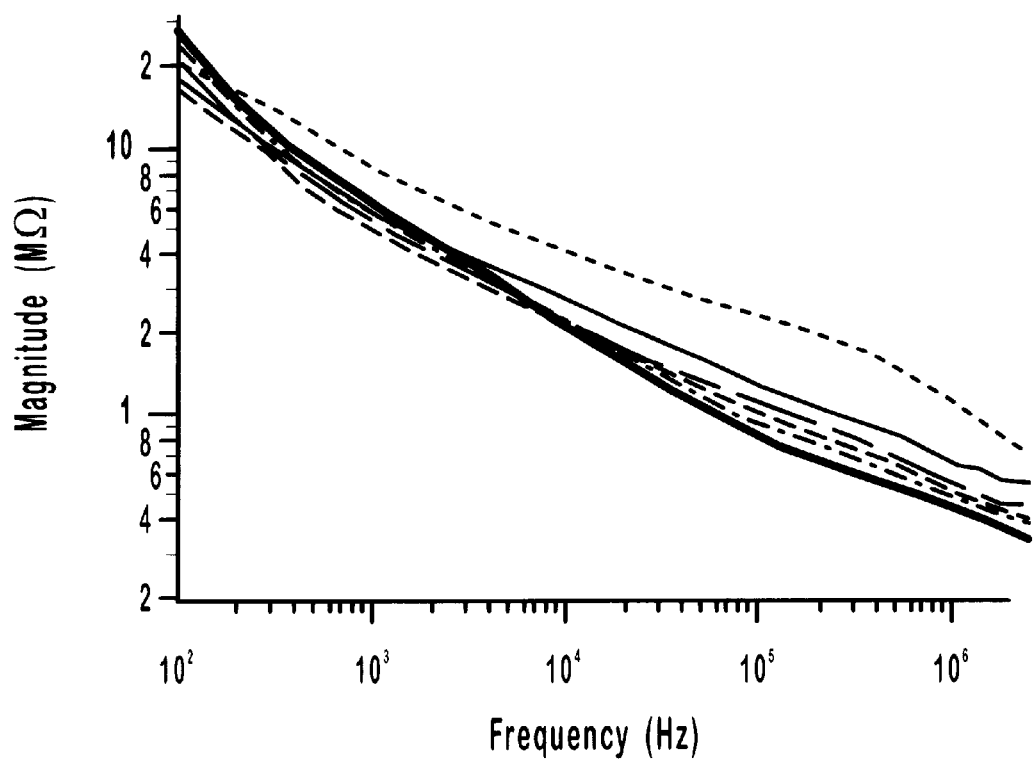
Figure 5F:
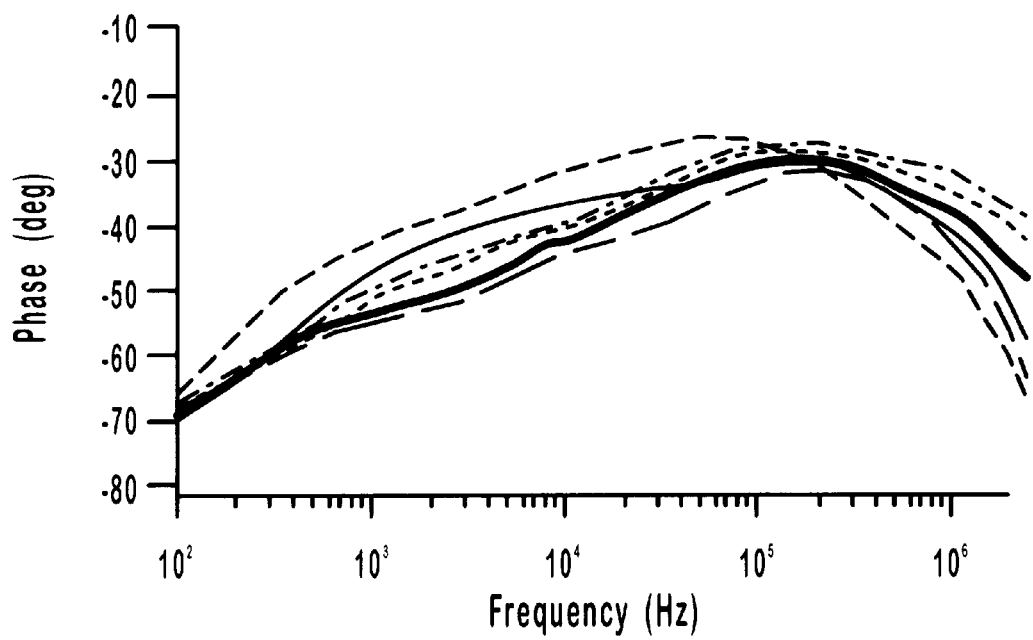

The electric impedance was also measured for individual polymorphonuclear leukocytes (PMNs) and erythrocytes (red blood cells, RBCs) placed in the microchannels of the MEI devices. The results are depicted in the graphs of FIGS. 5C and 5D for PMN, and FIGS. 5E and 5F for RBCs. Both the magnitude and phase of the impedance were highly repeatable between different cells. The dashed curves represent an average for PMN type I cells (n=9) and the solid curves indicate the average for PMN type II cells (n=19) in FIGS. 5C and 5D. Thick solid curves in FIGS. 5E and 5F indicate averages for the RBC population (n=50). Thin black solid and dashed curves are reproduced from FIGS. 5C and 5D for comparison of RBCs to PMNs.

Results of the electric impedance measurements for the PMNs indicate the presence of two distinct subpopulations. Averages for type I cells are shown in thick dashed lines and averages for type II cells are shown in thick solid lines in FIGS. 5C and 5D. It is possible that one of the groups of PMN cells were dead cells, since the permeability of cell membranes is known to decrease upon death. Another possibility to explain the data is that there are two types of leucocytes in the population. In either case, the results indicate the potential for the MEI devices for single-cell sorting and characterization. It should also be noted that the largest intercellular differences were recorded at the highest frequency tested of 2 MHz.

EXAMPLE 3

Microchannel devices for use in $\mu$-EFFF systems were fabricated by the following procedure. A 3 inch (76 mm) single-side polished silicon wafer (<100> crystallographic orientation) was put into a PE-CVD apparatus and a layer of silicon nitride having a thickness of 2500 Å was deposited on the polished side of the wafer. The silicon nitride was then patterned using photoresist as a mask on both sides of the wafer. Patterning was done such that 1 mm square openings were made in the silicon nitride on the unpolished side of the wafer in a $CF_4$ plasma. Bulk anisotropic etching was then performed in a 20% KOH solution at a temperature of 56° C. for a period of 24 hours to define the inlet and outlet ports. The KOH etching process left a thin silicon nitride membrane about 1000–2000 Å thick on the front polished side of the wafer. The openings on the polished side of the wafer were about 200 square $\mu$m.

Next, a layer of 1000 Å of titanium followed by a layer of 1500 Å of gold were sputtered onto the polished side of the wafer in order to form a channel electrode. This metallization layer was extended to the edge of the wafer where electrical connection was to be made for the channel electrode. The metals were then patterned to form a first channel electrode using a photoresist mask and an etchant mixture of 400 g of KI, 100 g of $I_2$, and 400 ml water, in order to etch the gold; and also a 1% BF solution to etch the titanium. A conductive adhesive was used to bond a wire directly to the wafer in the area of the electrode metallization to allow electrical contact.

Thick photosensitive polyimide micromolding (Amoco Ultradel 7505) was used to define the microchannels (10–40 $\mu$m in height) such that angled input and output flow regions were formed at opposite ends of each microchannel. The polyimide was spun onto the wafers and then placed onto a leveling plate for 15 minutes to ensure an even coating and to eliminate any potential thickness irregularities. After ultraviolet exposure and pattern development according to standard laboratory procedures, the polyimide was completely cured in an oven at a temperature of 350° C. for 6 hours.

The thin silicon nitride membrane was then removed using reactive ion etching (RIE) in a $CF_4$ plasma. A 1000 Å layer of titanium and a 1500 Å layer of gold were then sputtered onto a glass substrate that had been cut to fit over a group of the microsized channels. The titanium and gold layers on the glass substrate were subsequently patterned to form the second channel electrode.

The detector was fabricated on-chip by depositing 500 Å of titanium followed by 2500 Å of gold onto both the silicon substrate and the glass substrate that form the microchannel, and then using photoresist to pattern the detector electrodes. The detector electrode on the glass substrate was 100 $\mu$m in width while the detector electrode on the silicon wafer was 5, 25, or 100 $\mu$m in width. The width of the detector electrode on the glass substrate was kept at 100 $\mu$m to facilitate alignment with the other detector electrode, since alignment was done by hand under a microscope.

The glass and silicon substrates were then bonded together using a UV curable, biocompatible adhesive (3341 Medical Device Adhesive from Loctite). The glass substrate was pressed against the silicon substrate with the channel and detector electrodes aligned, while the UV adhesive was dispensed near the polyimide-glass interface and allowed to flow between the substrates due to capillary action. Once the adhesive had completely surrounded the channel, it was cured using a UV lamp. A conductive adhesive was then used to bond a wire to a contact pad on the glass substrate, thereby allowing a lead to be attached. Once the channels were assembled, leads were attached to the bond pads of the detector electrodes using a conductive adhesive to allow a good electrical connection.

Steel tubing with an inner diameter of 125 $\mu$m was attached to the silicon substrate over the inlet and outlet ports. Plastic ferrules from Upchurch Scientific were affixed using a UV curable adhesive to the surface of the silicon substrate directly over the inlet and outlet ports in order to localize the steel tubing on the ports.

The microchannel devices fabricated in accordance with the process described hereinabove had channels 4–6 cm in length, 20–30 $\mu$m in height, and 0.4–8 mm in width, with aspect ratios between 20 and 400.

EXAMPLE 4

Microchannel devices fabricated according to the procedure of Example 3 were tested for various characteristics. The microchannels used in these experiments were 6 mm in width and had a height of 26 $\mu$m. The ends of the microchannels tapered to the inlet and outlet ports at a 60° angle. All devices tested had a 25 $\mu$m detector electrode on the silicon substrate. Once the microchannel and detector were fabricated, they were connected to an HP 6128C DC Power Supply and an HP 3458A multimeter. The multimeter was connected to a PC for data collection and analysis using LabView software. Connections, sample injection, pumps, and other hardware were also implemented to form an operative $\mu$-EFFF system. The buffer solution used was deionized water for all experiments.

The experimental matrix took into account the variation of three basic parameters: buffer flow rate, applied voltage and corresponding current, and sample size and composition. Flow rates through the detector were varied from 0.1–2.0 mL/hr (0.017–0.33 cm/s), which is the typical range for most separations that might use this detector. Voltages applied to the detector electrodes were varied in the range between 2 and 8 V. For most detector characterization experiments the sample was acetone and was varied in concentration from 0% to 100%. The time constant, $\tau$, was also measured for a series of flow rates and voltages for comparison.

The results of the experimental testing of the microchannel devices are set forth below.

Figure 6A:
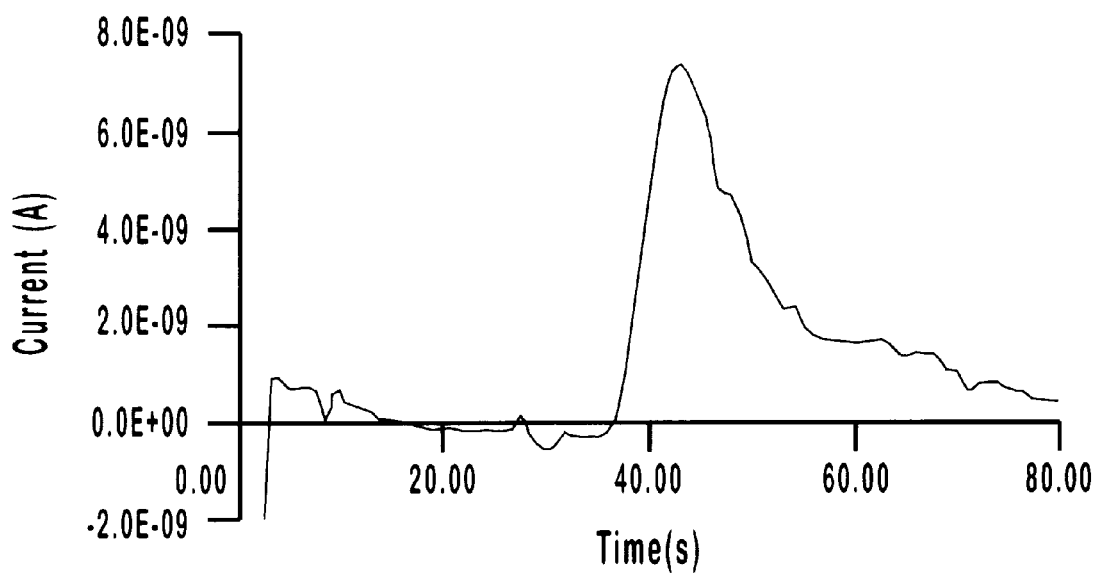
FIGS. 6A and 6B are graphs of the measured current as a function of time for an impedance detector of the invention.
Figure 6B:
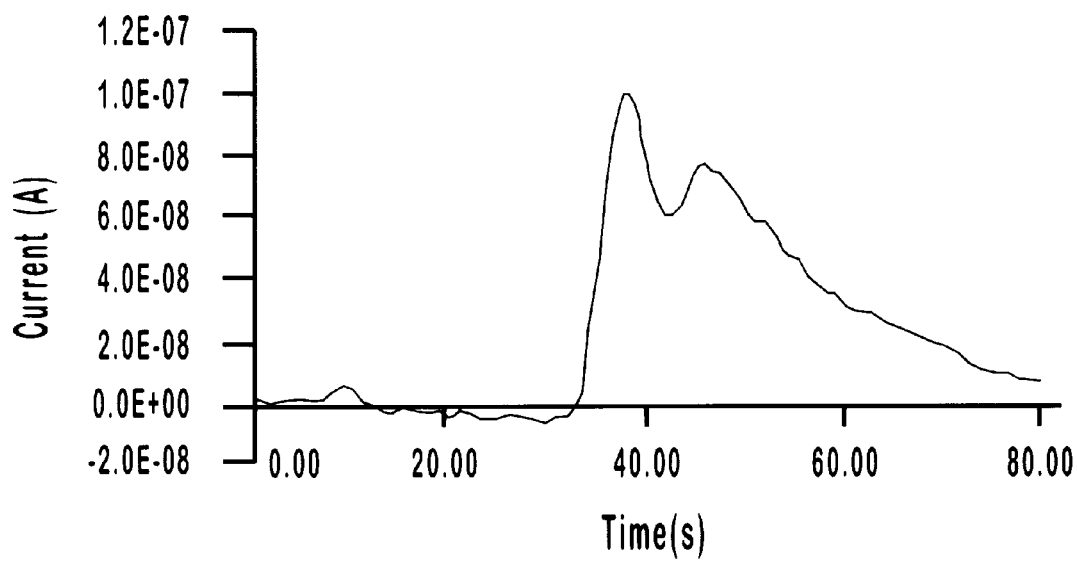

FIGS. 6A and 6B are graphs showing the measured current (in amps) plotted as a function of time (in seconds) for the on-chip detector. A typical acetone injection peak is shown in FIG. 6A, with a very fast initial response to the peak and a slower drop off or tailing on the backside of the peak. While this behavior is likely due to a high flow rate in the channel, the tailing is somewhat exaggerated and likely somewhat greater than reality due to the somewhat slower response of the detector in returning to a steady state current. The detector was fast enough though to detect a slight double injection as shown by the double peak in FIG. 6B, which was not detectable by an off-chip detector. The double peak was actually an artifact of the injection process, and can be eliminated through adjustment of the injection parameters. Thus, the on-chip detector is capable of resolving signals on a smaller timescale than an off-chip detector, which did not register a double peak under the same conditions.

Figure 7:
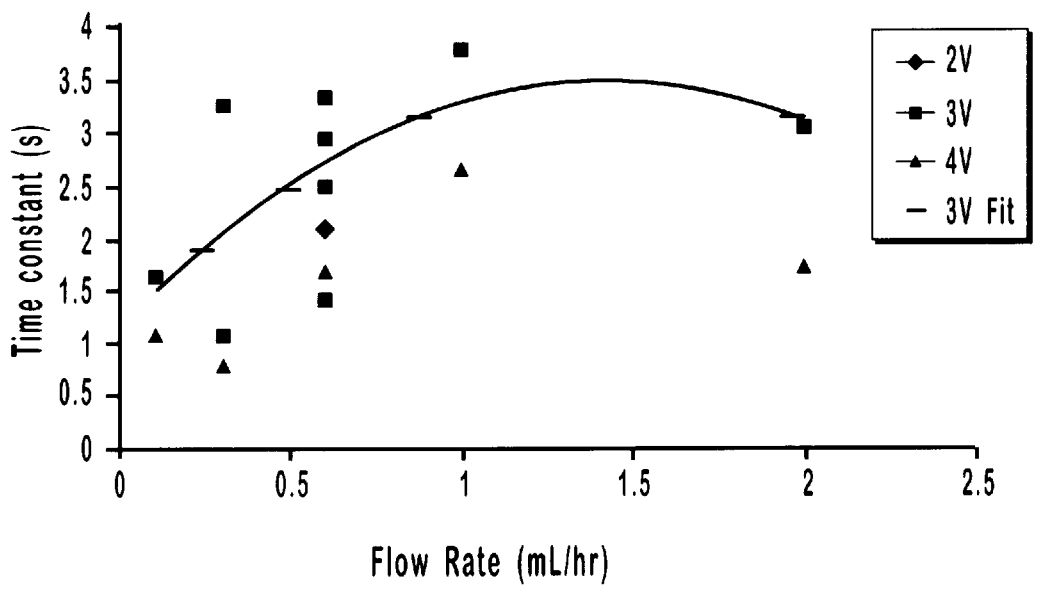
FIG. 7 is a graph of the time constants necessary to reach steady state for a series of flow rates and voltages for the detector of the invention.

FIG. 7 is a graph showing the time constant necessary to reach steady state for a series of flow rates and voltages for the on-chip detector in which 0.1 $\mu$L samples of acetone in a deionized water buffer were used as the input. The data was plotted for applied voltages of 2V, 3V, and 4V, with the corresponding flow rates indicated. It should also be noted that the time constants to reach steady state were higher for the system at 3 V than at 4 V. This indicates that it takes longer to reach steady state at 3 V. Also, at low flow rates the time constant is relatively low and slowly increases with flow rate before falling off again. The graph of FIG. 7 represents a combination of complex flow phenomena at work, but the general trend is that the time constant under typical conditions is approximately 4 seconds, which is sufficiently fast for most types of applications mentioned herein.

Figure 8:
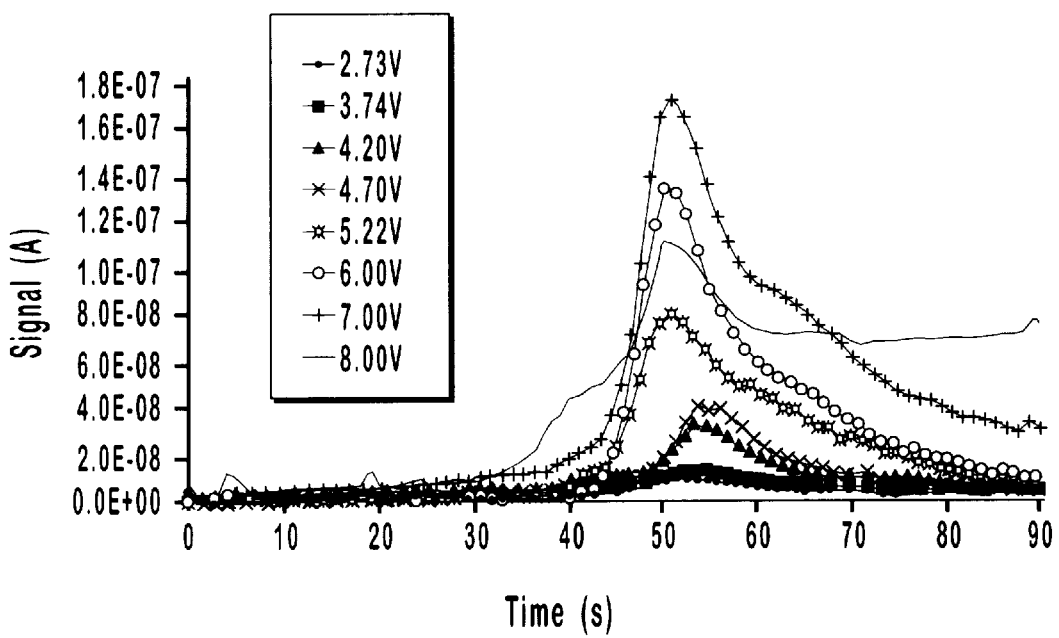
FIG. 8 is a graph showing superimposed data for sample runs at a variety of voltages for a detector of the invention.

The graph of FIG. 8 depicts several superimposed measurements for acetone sample runs at a variety of voltages for the on-chip detector. The runs were performed with identical samples and flow rates, but with varying applied voltages and corresponding baseline currents. The data show that the signal consistently grows with the voltage until the applied potential reaches 8V. At that point, electrolysis occurs and the current follows an exponential type of growth and is therefore not considered to be a useful range for the detector. It should be noted that every other run appears to return to a steady baseline, though the higher the voltage the longer it takes to get to baseline. There was also consistently low noise whose absolute magnitude was constant and insensitive to the applied voltage, suggesting that the noise is not a function of the applied voltage. As a consequence, the signal-to-noise ratio grows directly with the applied voltage.

Figure 9:
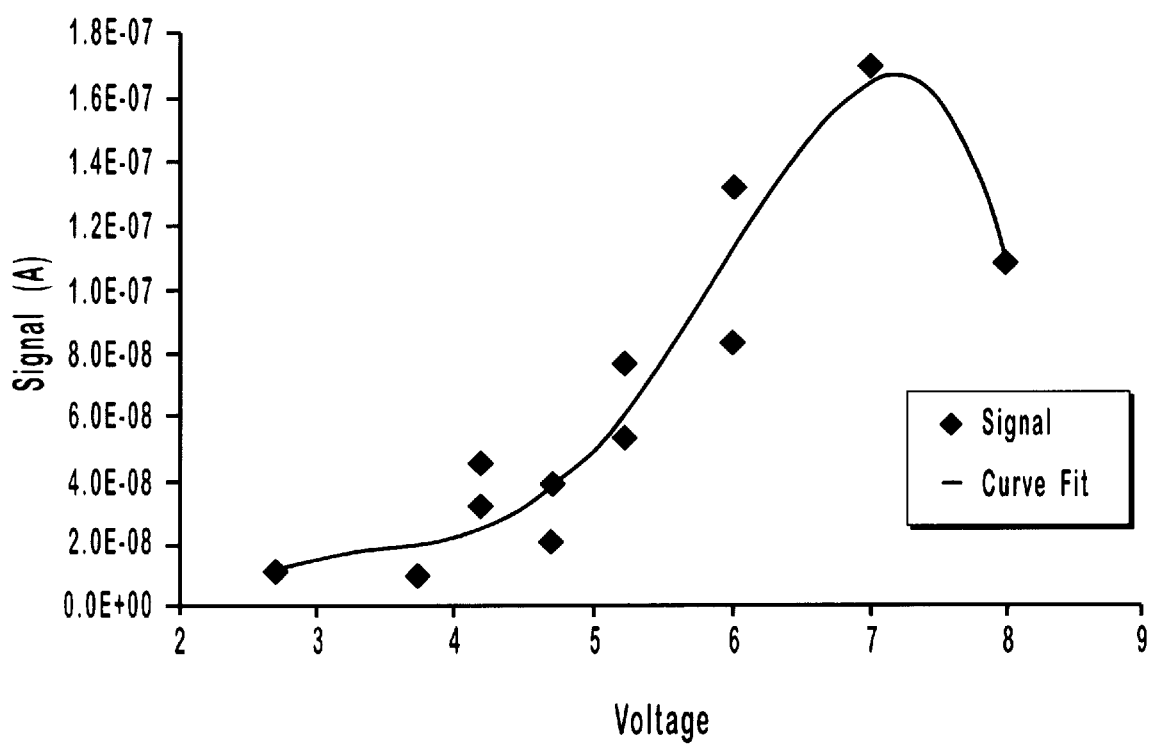
FIG. 9 is a graph showing the maximum signal obtained for sample runs with only a variation in voltage.

FIG. 9 is a graph showing the maximum signal obtained for the acetone test runs with only a variation in voltage. The growth in signal and the corresponding signal-to-noise ratio was quite dramatic. The relationship is clearly nonlinear, though there appears to be a range where it may be linear between 4 and 7V. It should be noted that at low voltages the signal begins to disappear, though even with applied voltages of 2.5 V, the signal-to-noise ratio is about 20 which is clearly enough for normal operation at high sample concentrations.

Figure 10:
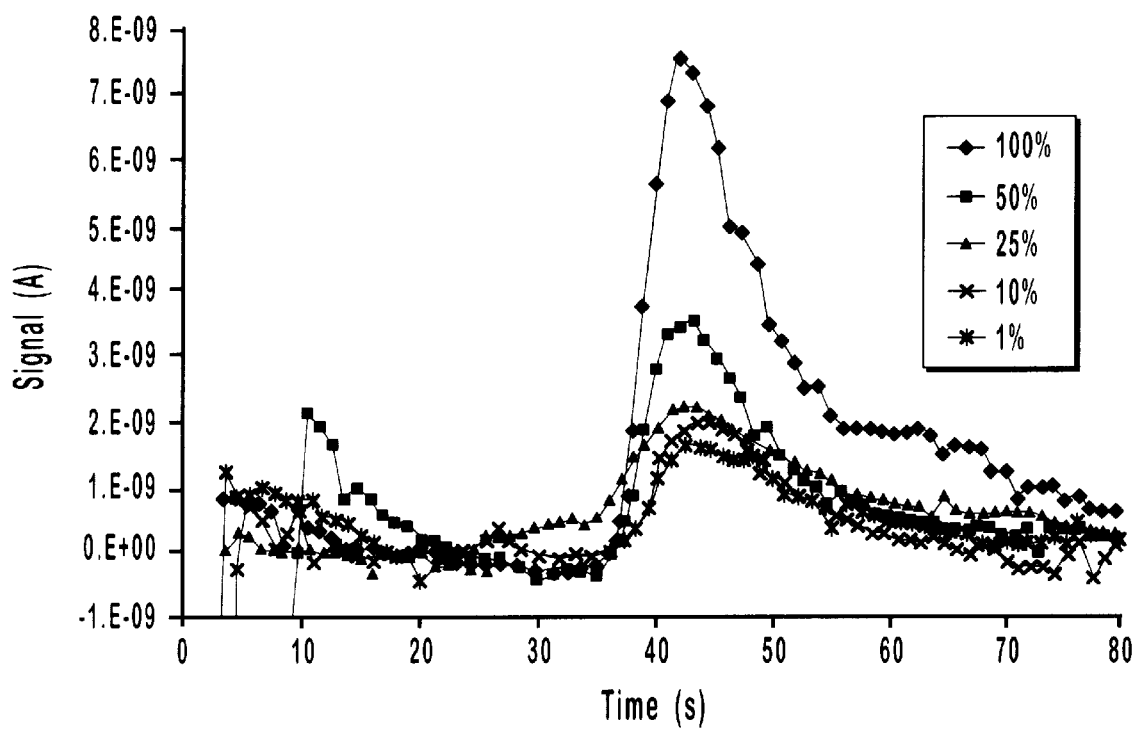
FIG. 10 is a graph showing superimposed data for signals measured by a detector of the invention for a variety of sample concentrations.
Figure 11:
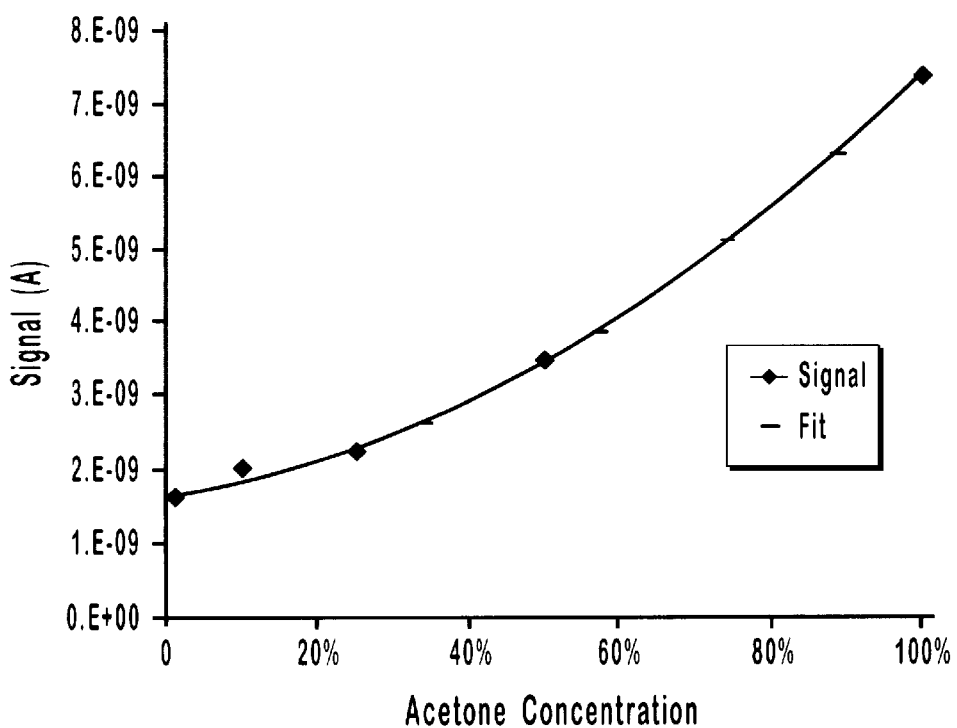
FIG. 11 is a graph showing how the signal measured by the detector of the invention varies with sample concentration.

The graph of FIG. 10 depicts superimposed data for signals measured by the on-chip detector for test runs with decreasing acetone concentrations. The data shows that the percentage of acetone in a constant sample volume does impact the response of the detector and thus concentration measurements can be quantitatively performed using the detector. FIG. 11 is a graph showing how the signal measured by the detector decreases with decreasing concentrations of acetone. Although the signal is not strictly linear, it is fairly close to linear and the data show that the detector is capable of detecting very small concentration differences. It is believed that the slight degree of nonlinearity may be corrected if the system is run at higher flow rates.

Figure 12:
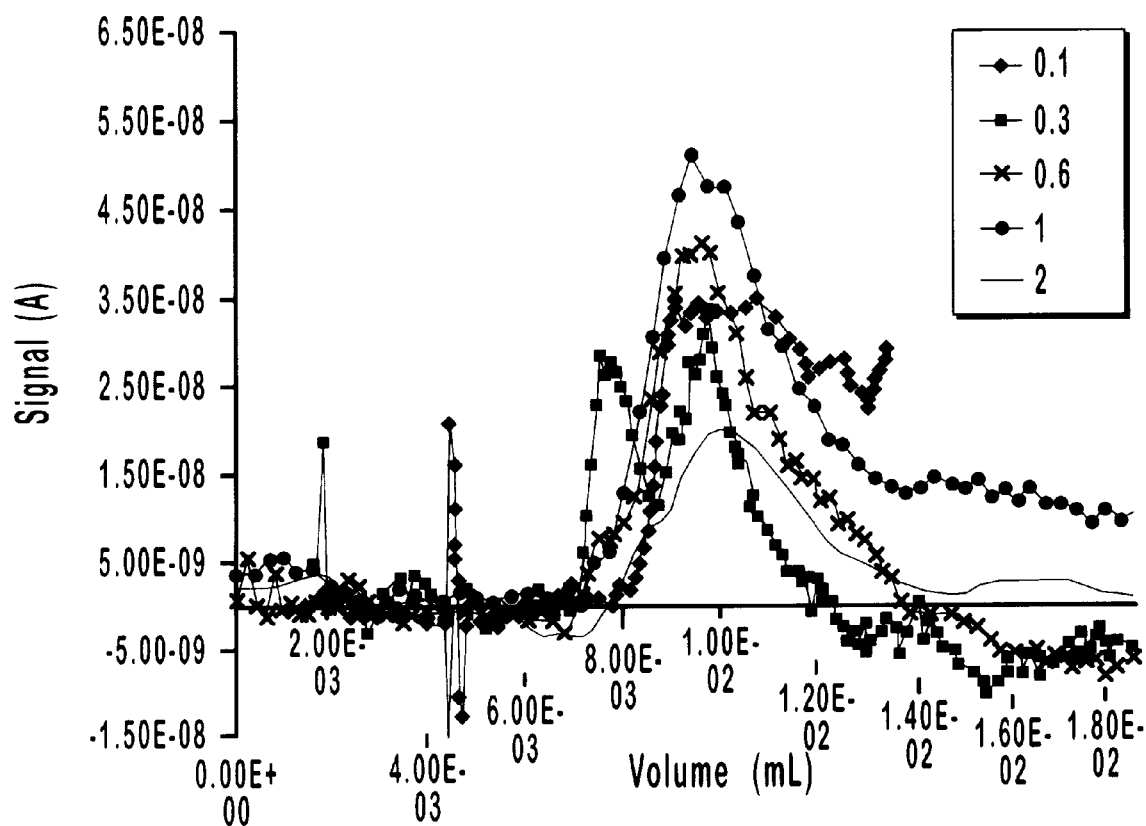
FIG. 12 is a graph showing several superimposed signals demonstrating how variations in flow rate affect the signal generated by the detector of the invention.

The graph of FIG. 12 shows several superimposed signals demonstrating how variations in flow rate affect the signal generated by the on-chip detector. The signal has a peak at about 1 mL/hr and drops off in both directions from there in a manner similar to that for time constants when compared by flow rate. The effect though is thought to be somewhat different. At high flow rates the residence time for the sample is very short so the net effect of the impedance change is reduced. At low flow rates, diffusion of the sample away from its center point plays a much greater role and the sample becomes diluted, again reducing the received signal. At a middle point, diffusion is minimized but the residence time in the detection area is still significant, allowing for an effective detection signal. Changes in the size of the detection wires may allow for better detection at high flow rates Considering the data presented above, it would appear that an optimal applied voltage for the on-chip detector used in this Example would be about 4 V, which would give increased signal strength without some of the instability problems of higher voltages. This value improves the time constant relative to lower voltages as well. The optimal flow rate appears to be about 0.6 mL/hr. While this value does not generate the lowest time constant or highest signal, it is a middle value that does not exacerbate problems with either of those parameters, but still provides a strong signal. In addition, the concentration of particles for any sample should be maximized to enjoy the greatest signal-to-noise ratio.

EXAMPLE 5

Microchannel devices fabricated according to the procedure of Example 3 and operatively implemented into a $\mu$-EFFF system as described in Example 4 were tested using the on-chip detector, as well as a conventional off-chip linear UV detector for a series of flow rates. Plate height measurements were carried out by injecting 100 nL samples of acetone into a system using the on-chip detector, and into a system using the off-chip detector. The width of the peaks was measured as well as the time required for the peak to elute. The plate height calculations were then performed using standard chromatography methods.

Figure 13:
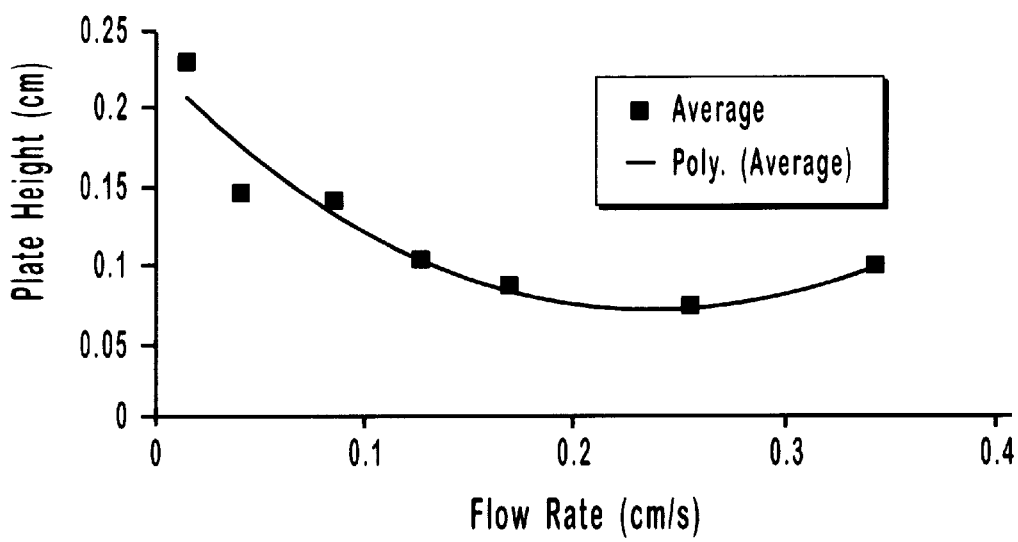
FIG. 13 is a graph of the effective plate heights as a function of flow rate for an off-chip detection system.

FIG. 13 is a graph of the effective plate heights as a function of flow rate for the off-chip detector. The graph shows increasing values of effective plate height at lower flow rates, indicating that diffusion is beginning to dominate at the lower flow rates. This effect was not observed with the on-chip detector. This can be interpreted as meaning that the diffusion must occur within the off-chip detector itself. The reason for the change in the relative importance of the diffusion is due to the large dimensions found in the off-chip detector compared to the channel itself. Thus, in miniaturized separation systems, the on-chip detector will provide more accurate results.

Figure 14:
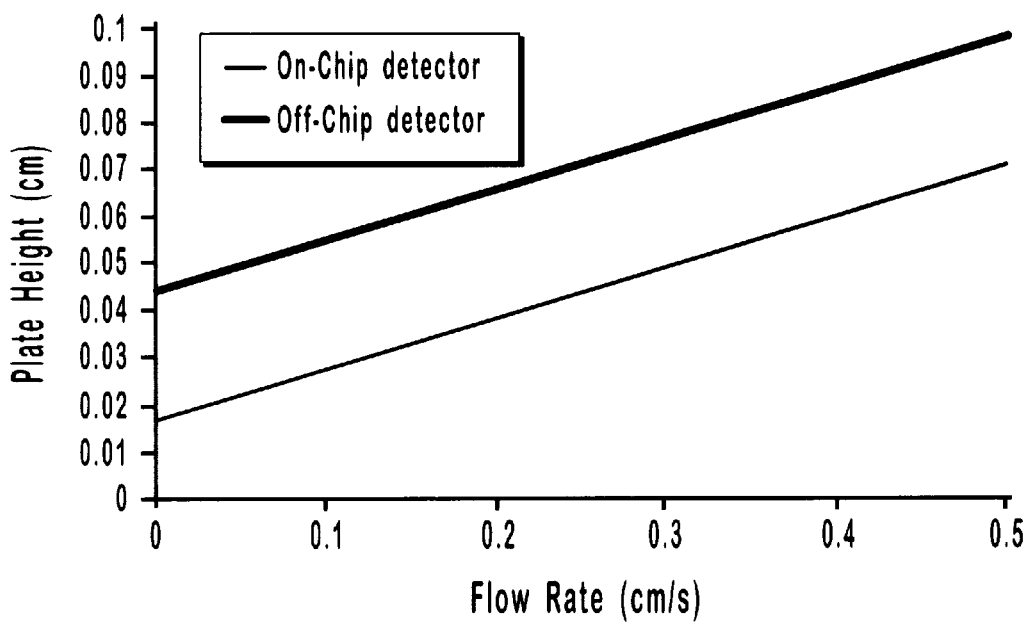
FIG. 14 is a graph of the effective plate heights as a function of flow rate for an on-chip detection system of the invention and an off-chip detection system.

The graph of FIG. 14 shows the effective plate heights as a function of flow rate for the on-chip detector and the off-chip detector showing the difference in band broadening. The data for the off-chip detector neglects the diffusion-affected data given in FIG. 13 for comparison. The y-intercept on the graph may be interpreted as the effective band broadening due to the instrument. The band broadening is reduced by more than half when the switch is made to the on-chip detector. The difference in the y-intercept can be considered as a measure of the degree of improvement.

Figure 15:
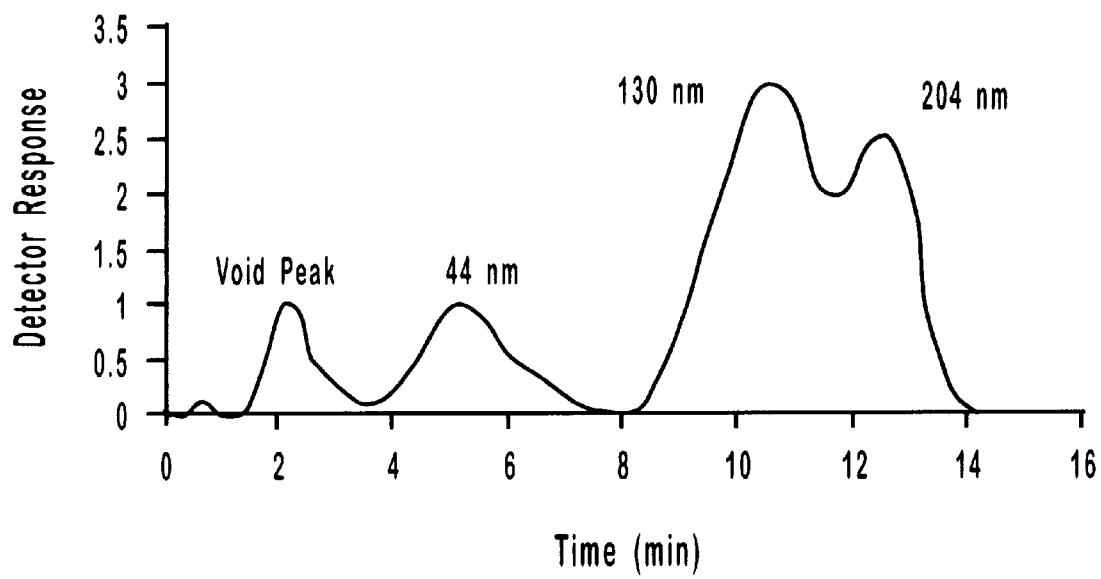
FIG. 15 is a graph of the detector response as a function of time for an off-chip detection system.
Figure 16:
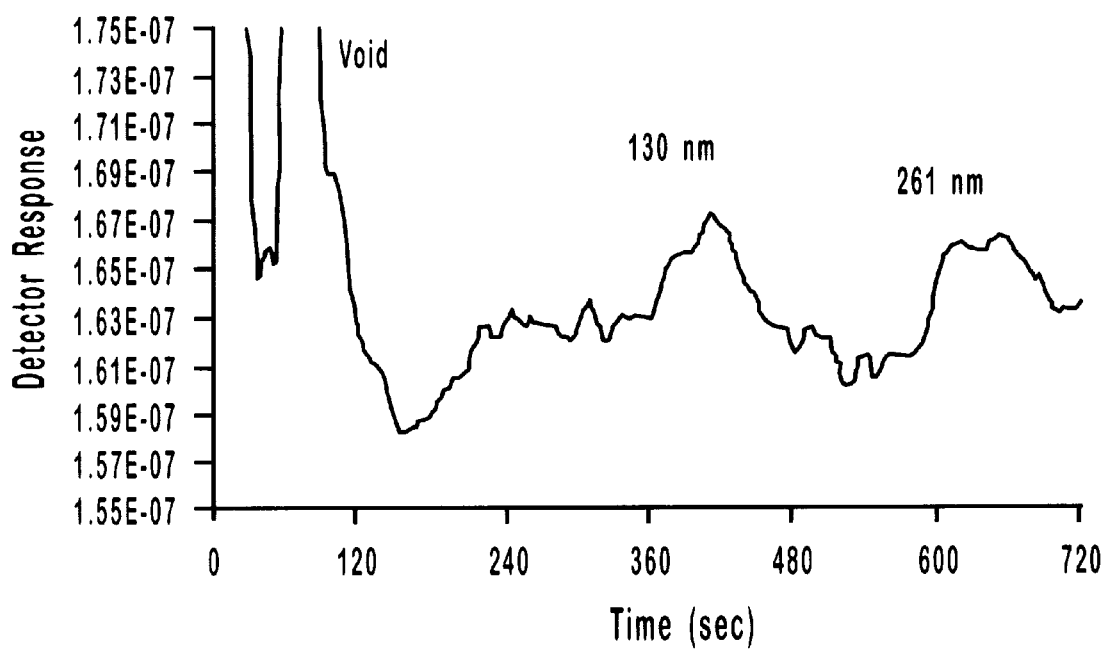
FIG. 16 is a graph of the detector response as a function of time for an on-chip detection system of the invention.

FIG. 15 is a graph of the detector response as a function of time for the off-chip detector in a $\mu$-EFFF system for sample runs to separate particles having diameters of 44 nm, 130 nm, and 204 nm. The flow rate used was 0.6 mL/hr and the current was 170 $\mu$A. FIG. 16 is a graph of the detector response as a function of time for the on-chip detector in a $\mu$-EFFF system for sample runs to separate particles having diameters of 130 nm and 261 nm. The flow rate used was 0.6 mL/hr and the current was 173 $\mu$A.

A comparison of the graphs of FIGS. 15 and 16 show improved separation time for the on-chip detector and more clearly resolved peaks. The resolution for the on-chip detector is at least 50% higher than for the off-chip detector, consistent with the plate height data. While the noise level as shown in FIG. 16 is somewhat higher due to the electric field in the channel associated with the operation of the separation system, the peaks for the various particles are clearly distinguished and easily measured. One significant advantage of the on-chip detector is that it quickly goes to baseline when power is applied (typically less than 10 seconds) meaning that the detector could be turned on even after the sample has been injected into the system.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for monitoring a test sample in a micro-analysis system, comprising the steps of:
   providing a micro-electric sensor device in a micro-analysis system, the micro-electric sensor device comprising:
      a substrate having a substantially planar upper surface;
      at least one microchannel formed in the upper surface of the substrate and defined by a pair of opposing sidewalls and a bottom wall in the substrate;
      one or more reservoirs formed in the planar surface of the substrate and in fluid communication with the microchannel; and
      at least one pair of opposing electrodes on the planar surface of the substrate and terminating at electrode tips formed on the opposing sidewalls of the microchannel such that the electrode tips face each other, thereby creating a detection zone in the microchannel between and adjacent to the electrodes;
   supplying electrical power to the electrodes to create an electric field in the detection zone of the microchannel;
   injecting a test sample into the microchannel; and
   detecting changes in the electric field as the test sample enters the detection zone of the microchannel to provide conductivity or impedance based measurements of the test sample in the microchannel.

2. The method of claim 1, wherein the test sample comprises a particulate-containing fluid.

3. The method of claim 1, wherein the test sample comprises a biological material.

4. The method of claim 1, wherein the measurements of the test sample are provided by directing a signal from the electrodes to a processing device for analyzing the signal.

5. The method of claim 4, further comprising the step of displaying or printing data generated by the processing device.

6. A micro-electric sensor device for use in a micro-analysis system, comprising:
   a substrate having a substantially planar upper surface;
   at least one microchannel formed in the upper surface of the substrate and defined by a pair of opposing sidewalls and a bottom wall in the substrate;
   one or more reservoirs formed in the planar surface of the substrate and in fluid communication with the microchannel; and
   at least one pair of opposing electrodes on the planar surface of the substrate and terminating at electrode tips formed on the opposing sidewalls of the microchannel such that the electrode tips face each other, thereby creating a detection zone in the microchannel between and adjacent to the electrodes;
   wherein the electrodes provide for transverse interrogation of a test sample in the microchannel by conductivity or impedance based measurements.

7. The sensor device of claim 6, further comprising a processing means operatively connected to the electrodes for analyzing a signal from the electrodes.

8. The sensor device of claim 7, wherein the processing means is a network analyzer.

9. The sensor device of claim 7, further comprising an output device operatively connected to the processing means for displaying or printing data generated by the processing means.

10. The sensor device of claim 6, wherein the device has a pair of opposing reservoirs in fluid communication with the microchannel at opposite ends thereof.

11. The sensor device of claim 10, wherein the device has a plurality of additional reservoirs in fluid communication with the microchannel.

12. The sensor device of claim 11, wherein the device has plurality of opposing electrode pairs on the planar surface of the substrate that terminate in electrode tips formed on the opposing sidewalls of the microchannel.

13. The sensor device of claim 6, wherein the microchannel is dimensioned such that the distance between the opposing sidewalls along the length of the microchannel is less than about 100 $\mu$m.

14. The sensor device of claim 6, further comprising a cover plate attached to the upper surface of the substrate so as to form a top wall for the microchannel.

15. The sensor device of claim 14, wherein the microchannel is dimensioned such that the distance between the bottom wall and the top wall along the length of the microchannel is less than about 100 $\mu$m.

16. The sensor device of claim 14, wherein the microchannel has a cross sectional area of about 15 $\mu m^2$ to about 300 $\mu m^2$ in the detection zone.

17. The sensor device of claim 14, wherein the microchannel has an aspect ratio of width to height of about 1:1 or greater.

18. The sensor device of claim 14, wherein the microchannel has a transverse cross-sectional profile that is substantially rectangular.

19. The sensor device of claim 14, wherein the cover plate has one or more openings therein providing access to the one or more reservoirs in the substrate.

* * * * *

UNITED STATES PATENT AND TRADEMARK OFFICE
CERTIFICATE OF CORRECTION

PATENT NO.   : 6,169,394 B1
DATED        : January 2, 2001
INVENTOR(S)  : A. Bruno Frazier, Richard D. Rabbitt and H. Edward Ayliffe It is certified that error appears in the above-identified patent and that said Letters Patent is hereby corrected as shown below:

Column 1,
Line 3, insert the following paragraph:
-- This invention was made with government support under grant nos. WU9628 and WU9733 awarded by the National Institute of Health. The Government has certain rights to this invention. --

Column 2,
Line 11, before "in providing additional" change "usefull" to -- useful --
Line 12, before "properties of cells" change "capacititve" to -- capacitive --

Column 3,
Line 25, after "to achieve the" change "forgoing" to -- foregoing --
Line 59, after "on-chip according" insert -- to --

Column 6,
Line 22, after "can be formed" change "form" to -- from --

Column 7,
Line 3, after "through microchannel" change "22" to -- 12 --
Line 54, after "opposing sidewalls" change "37" to -- 36 --

Column 9,
Line 63, after "combinations thereof" insert -- . -- (period)

Column 11,
Line 29, after "by measuring the" change "currently" to -- current --

Column 12,
Line 61, after "systems, as" change "wells" to -- well --

Column 13,
Line 41, before "gold seed" change "andlor" to -- and/or --

Column 15,
Line 20, before "solution" change "BF" to -- HF --

UNITED STATES PATENT AND TRADEMARK OFFICE
CERTIFICATE OF CORRECTION

PATENT NO. : 6,169,394 B1
DATED : January 2, 2001
INVENTOR(S) : A. Bruno Frazier Richard D. Rabbitt and H. Edward Ayliffe It is certified that error appears in the above-identified patent and that said Letters Patent is hereby corrected as shown below:

<u>Column 20,</u>
Line 25, after "the device has" insert -- a --

Signed and Sealed this

First Day of April, 2003

JAMES E. ROGAN
*Director of the United States Patent and Trademark Office*